United States Patent
Hopper et al.

(10) Patent No.: US 10,472,949 B2
(45) Date of Patent: Nov. 12, 2019

(54) GAS-IN-SOLUTION DETECTION SYSTEM AND METHOD

(71) Applicant: Cameron International Corporation, Houston, TX (US)

(72) Inventors: Hans Paul Hopper, Aberdeen (GB); Emanuel Gottlieb, Upper St. Clair, PA (US); Omar M. Kabir, Waller, TX (US)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 255 days.

(21) Appl. No.: 15/419,681

(22) Filed: Jan. 30, 2017

(65) Prior Publication Data

US 2018/0217101 A1    Aug. 2, 2018

(51) Int. Cl.
*G01N 29/02*    (2006.01)
*E21B 47/06*    (2012.01)
*E21B 49/08*    (2006.01)

(52) U.S. Cl.
CPC .............. *E21B 47/06* (2013.01); *E21B 49/08* (2013.01); *G01N 2291/02433* (2013.01)

(58) Field of Classification Search
None
See application file for complete search history.

(56) References Cited

U.S. PATENT DOCUMENTS

| | | |
|---|---|---|
| 2,279,254 A | 4/1942 | Irwin |
| 4,235,099 A | 11/1980 | Ishizaka |
| 4,522,068 A | 6/1985 | Smith |
| 4,580,444 A | 4/1986 | Abts et al. |
| 4,892,383 A | 1/1990 | Klainer et al. |
| 6,640,900 B2 | 11/2003 | Smith |
| 7,578,350 B2 | 8/2009 | Cooper et al. |
| 8,495,913 B2 | 7/2013 | Partington et al. |
| 2003/0029228 A1* | 2/2003 | Bloder ............... G01N 7/14 73/53.01 |
| 2003/0134426 A1* | 7/2003 | Jiang ................. E21B 47/011 436/121 |

(Continued)

OTHER PUBLICATIONS http://www2.emersonprocess.com/enUS/news/pr/Pages/1505RoxarWetgasMeter.aspx, Emerson launches subsea wet gas meter to reduce risk and strengthen production optimization strategies, News Release, May 5, 2015, Emerson, Stavanger, Norway.

(Continued)

*Primary Examiner* — Paul M. West
*Assistant Examiner* — Mark A Shabman
(74) *Attorney, Agent, or Firm* — Helene Raybaud

(57) ABSTRACT

A fluid monitoring system includes, a channel having a first end configured to be fluidly coupled to a first portion of a conduit of a mineral extraction system to enable fluid to flow from the conduit into the channel and a second end configured to be fluidly coupled to a second portion of the conduit to enable return of the fluid from the channel into the conduit. The system also includes an actuator assembly positioned along the channel and configured to isolate a portion of the fluid within a chamber of the actuator assembly. The actuator assembly is configured to expand a volume of the chamber to reduce a pressure while the portion of the fluid is within the chamber to facilitate identification of an indicator of dissolved gas within the fluid.

20 Claims, 17 Drawing Sheets

(56) References Cited

U.S. PATENT DOCUMENTS

2015/0361742 A1   12/2015  Gottlieb et al.
2016/0215608 A1    7/2016  Jaffrey

OTHER PUBLICATIONS

Molz, Eric, et al., Ultrasonic Velocity and Attenuation Measurements in High Density Drilling Muds, SPWLA 39th Annual Logging Symposium, May 26-29, 1998, 19 pgs, Houston, TX, US.
Hayman, A. J., Ultrasonic Properties of Oil-Well Drilling Muds, 1989 Ultrasonics Symposium, pp. 327-332, IEEE, Clamart, France.
U.S. Appl. No. 15/154,748, filed May 13, 2016, Andrew Jaffrey.
U.S. Appl. No. 15/270,261, filed Sep. 20, 2016, Hans Paul Hopper.

\* cited by examiner

US 10,472,949 B2

GAS-IN-SOLUTION DETECTION SYSTEM AND METHOD

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Natural resources, such as oil and gas, are used as fuel to power vehicles, heat homes, and generate electricity, in addition to various other uses. Once a desired resource is discovered below the surface of the earth, drilling and production systems are often employed to access and extract the resource. These systems may be located onshore or offshore depending on the location of a desired resource. Further, such systems generally include numerous fluid conduits to contain and/or to direct fluids, such as drilling mud, production fluid, or the like during drilling and extraction operations.

BRIEF DESCRIPTION OF THE DRAWINGS

Various features, aspects, and advantages of the present disclosure will become better understood when the following detailed description is read with reference to the accompanying figures in which like characters represent like parts throughout the figures, wherein.

DETAILED DESCRIPTION OF SPECIFIC EMBODIMENTS

Figure 1:
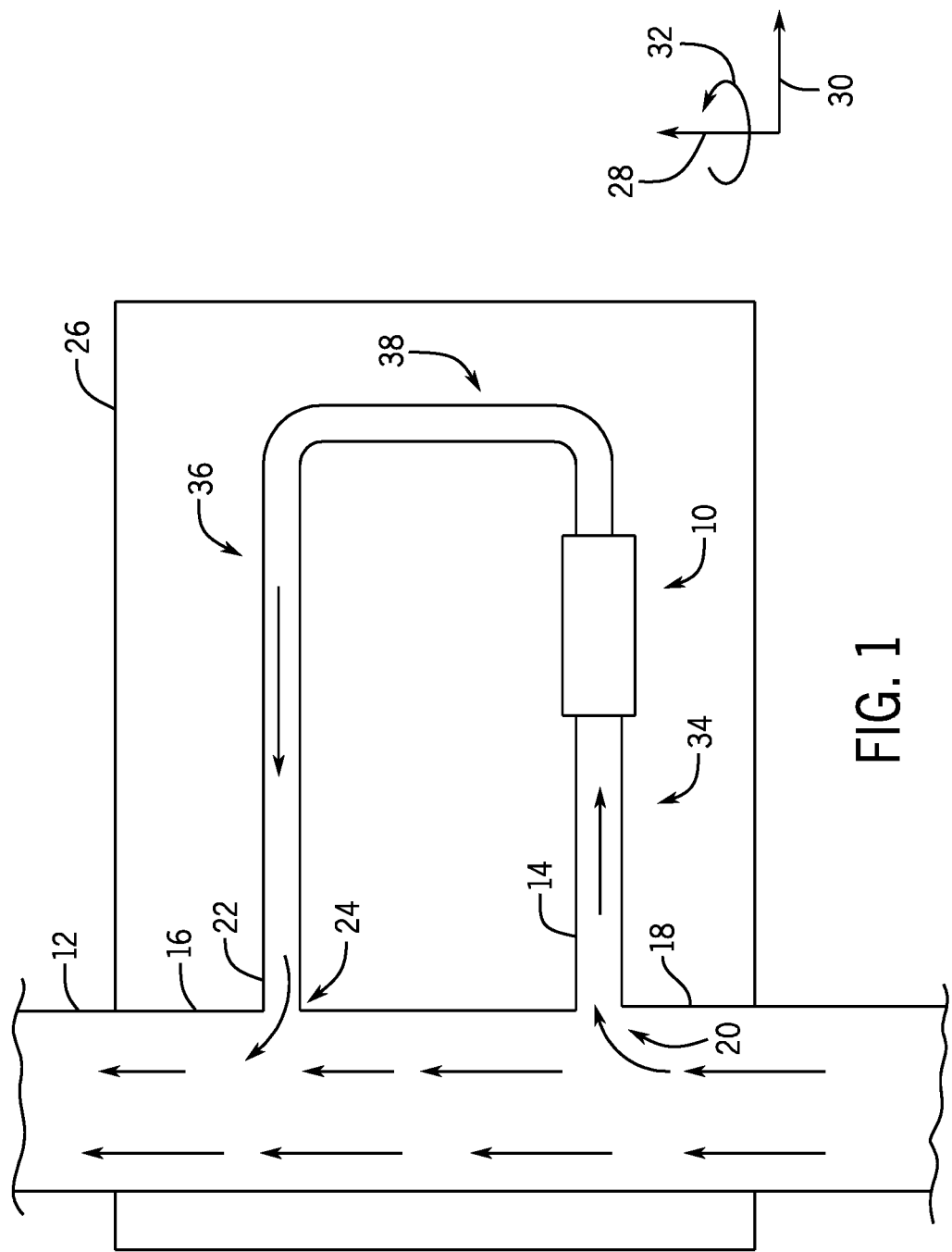
FIG. 1 is a schematic diagram of a gas-in-solution detection system (GISDS) coupled to a fluid conduit, in accordance with an embodiment of the present disclosure.

One or more specific embodiments of the present disclosure will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments relate generally to a gas-in-solution detection system (GISDS) that may be used to detect gas-in-solution (e.g., dissolved gas or gas dissolved in a liquid) within a conduit (e.g., fluid conduit or passageway) of a drilling system and/or a production system. Knowledge of parameters of fluid (e.g., formation fluid) flowing to the surface is useful for efficient operation and subsequent handling of the fluid. An important factor when controlling and containing fluids that could contain hydrocarbons is a possible change in state from a liquid to a gas in the fluid mixture. Under pressure, hydrocarbon liquids can contain gas-in-solution. Such liquids may be designated as saturated liquids, and gas-in-solution is generally undetectable in a pressurized liquid. Formation fluid entering a wellbore can be a mixture of various unknown constituents, such as elements of gas, oil, water, as well as any circulated or injected fluids. It is therefore desirable to identify parameters of the fluid as early as possible (e.g., at a subsea location or upstream location) and to identify parameters, especially gas-in-solution (e.g., an indicator or a resultant of gas-in-solution) and/or free gas, before a change in state or phase change occurs (e.g., before the gas-in-solution changes from a liquid state to a gas state), such as due to changes in pressure as the fluid flows through the drilling system and/or production system. The point of phase change may be designated as a bubble point of the fluid. More particularly, the bubble point relates to a relationship point between temperature and pressure at which bubbles (e.g., gas) are formed in a certain liquid, and such a fluid may be designated as an unsaturated fluid. In a system that experiences an unsaturated occurrence (e.g., bubbles form in a liquid), the bubbles may coalesce into gas pockets and/or into gas slugs, which may disrupt the flow of liquid (e.g., into a chaotic state), which may be designated as a "kick" in drilling operations and "slugging" in production operations, for example.

In certain embodiments, the GISDS may include a channel (e.g., fluid conduit or passageway), one or more sensors (e.g., a pressure sensor, a temperature sensor, an acoustic sensor, or the like) configured to monitor respective characteristics of the fluid, an actuator assembly (e.g., piston assembly), one or more valves, a flow control device (e.g., a pump), a filter, and/or a flush system, for example. In certain embodiments, a first end of the channel may be fluidly coupled to a first portion of the conduit to enable fluid flow from the conduit into the channel and a second end of the channel may be fluidly coupled to a second portion of the conduit to enable return of the fluid from the channel into the conduit. At least one valve may be positioned proximate to the first end of the channel and/or at least one valve may be positioned proximate to the second end of the channel to adjust fluid flow from the conduit and/or through the channel.

The channel may extend through or be coupled to the one or more sensors and/or the piston assembly. Thus, as the fluid flows through the channel and/or experiences a pressure change within a chamber of the piston assembly, the one or more sensors may monitor respective characteristics (e.g., parameters) of the fluid that are indicative of gas-in-solution within the fluid. In some embodiments, the one or more sensors may be configured to monitor and to generate signals indicative of a pressure, a temperature, and/or attenuation of acoustic waves associated with the fluid, for example. In some embodiments, the pump may be used to facilitate fluid flow within the channel and/or to adjust a flow rate of the fluid through the channel, the filter may capture debris flowing through the channel, and/or the flush system may be used to provide a flush fluid to flush and/or clean the channel, filters, and/or other components of the GISDS. Thus, in operation, the GISDS may divert or extract fluid from the conduit into the channel, use one or more sensors and/or the piston assembly to monitor respective characteristics of the fluid to detect gas-in-solution, and subsequently return the fluid to the conduit. It should be understood that the systems and methods disclosed herein may be adapted to monitor any of a variety of fluids, such as any type of produced fluids, extracted fluids, supplied fluids, injected fluids, mud, water, steam, oil, gases, or the like, in any type of drilling and/or production system. Furthermore, the systems and methods disclosed herein may be adapted for use with any of a variety of conduits within drilling and/or production systems, such as a riser, a choke line, a kill line, or any suitable pipeline or conduit that supports a fluid. In some embodiments, the GISDS may include or be utilized in combination with various other sensors and/or monitoring systems (e.g., a fluid-analysis monitoring system [FAMS]) configured to monitor a conductivity, a capacitance, a dielectric constant, a chemical level (e.g., a carbon dioxide level or gas composition), absorption of light and/or energy, a density, a viscosity, a free gas content, an oil content, and/or a water content of the fluid, for example.

Certain systems for monitoring characteristics of fluids within drilling and/or production systems may include sensors positioned directly within the conduit. However, such systems may not reliably detect gas-in-solution and/or may be incapable of monitoring characteristics of the fluid within the conduit during certain drilling operations, such as when physical structures are positioned within the conduit (e.g., when a drill string is positioned within a riser, during casing installation, or the like). Furthermore, such systems may not accurately or reliably monitor characteristics of the fluid within the conduit due to uncontrolled, unknown, inappropriate, and/or varying flow rates (e.g., turbulent flow, stagnant, etc.) and/or because a distance across the conduit may be inappropriate (e.g., for transmitter and receiver pairs that exchange signals across the conduit). Advantageously, the GISDS may detect gas-in-solution and enable fluid monitoring regardless of obstructions or physical structures within the conduit and/or regardless of fluid flow rates within the conduit.

The GISDS may be configured to isolate fluid within the chamber of the piston assembly and to adjust the volume of the chamber to facilitate detection of gas-in-solution. In particular, the GISDS may increase the volume of the chamber, thereby decreasing the pressure within the chamber and enabling gas-in-solution to transition to free gas, which may be detectable via various sensors. Furthermore, the GISDS may control a flow rate of the fluid within the channel and/or contain a sample of the fluid within the chamber to enable each sensor to accurately and reliably monitor the respective characteristic, for example. The GISDS may also enable real-time monitoring and/or monitoring at generally remote or inaccessible locations, such as subsea locations, for example. Such a configuration may enable identification of changes to the fluid or undesirable characteristics of the fluid (e.g., gas-in-solution) in real-time or more quickly (e.g., as compared to systems that monitor the fluid at surface locations or downstream locations), thereby improving efficiency and operation of the drilling and production system, for example.

With the foregoing in mind, FIG. 1 is a schematic diagram of a gas-in-solution detection system (GISDS) 10 coupled to a conduit 12 (e.g. fluid conduit or passageway), in accordance with an embodiment of the present disclosure. As discussed in more detail below, the conduit 12 may be any of a variety of fluid conduits configured to support a fluid in a mineral extraction system (e.g., drilling system and/or a production system).

As shown, a channel 14 is fluidly coupled to the conduit 12 and extends from a radially-outer surface 16 (e.g., annular surface or side wall) of the conduit 12. In this illustrated embodiment, the channel 14 includes a first end 18 that is fluidly coupled to a first portion 20 of the conduit 12 and a second end 22 that is fluidly coupled to a second portion 24 of the conduit 12. In operation, fluid from the conduit 12 may pass into the channel 14 via the first end 18, flow through the GISDS 10, and subsequently return to the conduit 12 via the second end 22. As discussed in more detail below, the GISDS 10 may include one or more isolation assemblies (e.g., valves) to control flow of the fluid into and out of the GISDS 10 and/or the GISDS 10 may include one or more piston assemblies and one or more sensors to monitor respective characteristics (e.g., parameters) of the fluid as the fluid flows through the GISDS 10. In some embodiments, the channel 14 extends into and through the GISDS 10, and the channel 14 and/or the other components of the GISDS 10 are formed within and/or supported within a housing 26 (e.g., GISDS housing). In some embodiments, the housing 26 may be configured to be coupled (e.g., removably coupled, such as via fasteners, fixedly attached, such as via welded joints, or integrated within) to the conduit 12 and/or to other structures proximate to the conduit 12 to fluidly couple the channel 14 and the GISDS 10 to the conduit 12.

To facilitate discussion, the GISDS 10 and other components may be described with reference to an axial axis or direction 28, a radial axis or direction 30, or a circumferential axis or direction 32. In the illustrated embodiment, the conduit 12 extends along the axial axis 28, and the channel 14 has a generally u-shaped cross-section having a first portion 34 and a second portion 36 that extend along the radial axis 30 and are generally crosswise (e.g., perpendicular) to the conduit 12, and a third portion 38 that extends along the axial axis 28 and joins to the first portion 34 and the second portion 36 to one another. However, it should be understood that the channel 14, may have any suitable geometry that enables extraction of the fluid from the conduit 12, flow of the fluid through the GISDS 10, and subsequent return of the fluid to the conduit 12. Furthermore, while the GISDS 10 is illustrated along the first portion 34 of the channel 14, it should be understood that the various components of the GISDS 10 may be positioned at any suitable location between the ends 18, 22 of the channel 14.

Figure 2:
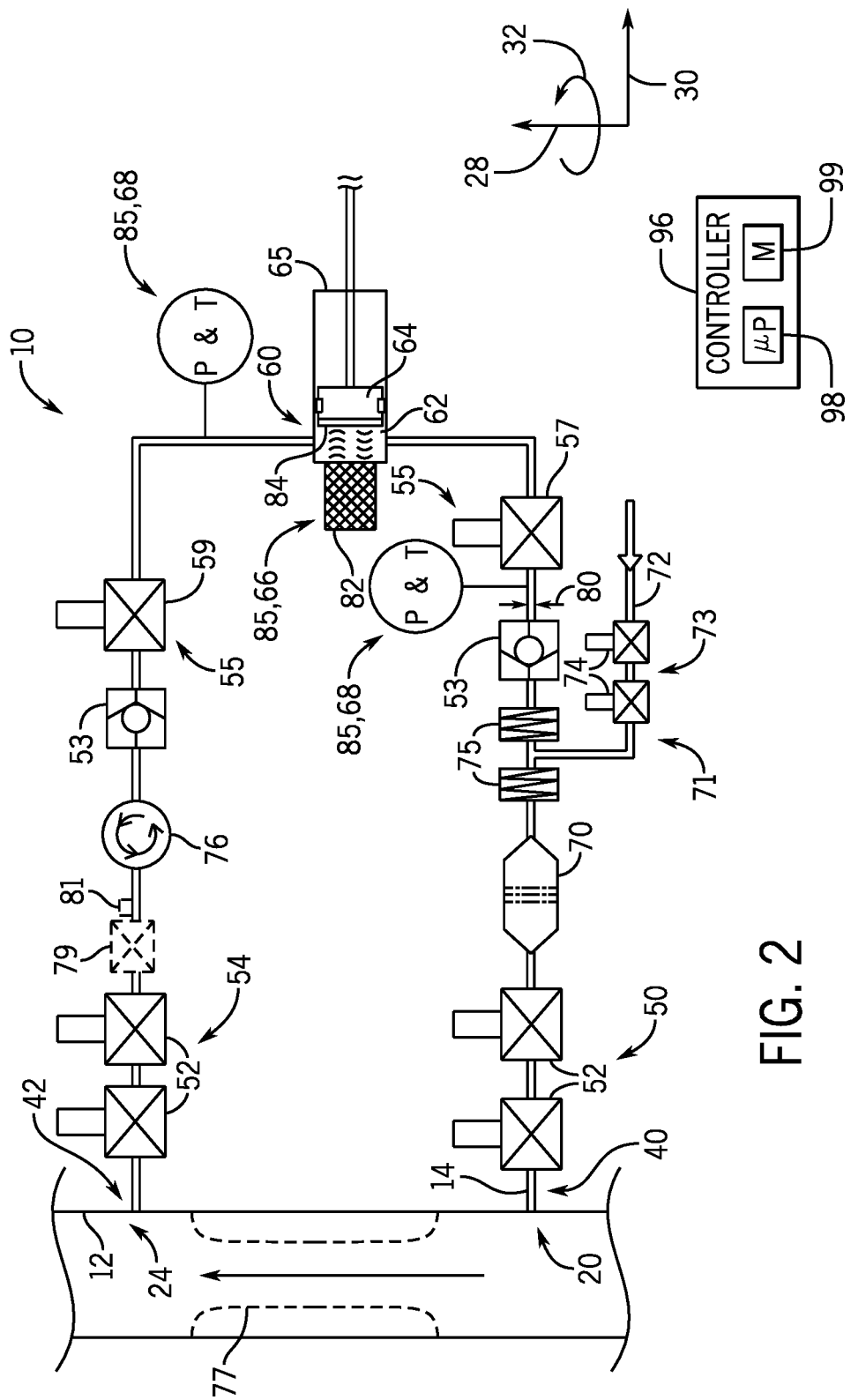
FIG. 2 is a schematic diagram of the GISDS, in accordance with an embodiment of the present disclosure.

FIG. 2 is a schematic diagram of the GISDS 10, in accordance with an embodiment of the present disclosure. In operation, the fluid may flow into a first end 40 (e.g., upstream end) of the GISDS 10 via the channel 14 and may exit a second end 42 (e.g., downstream end) of the GISDS 10 via the channel 14. As shown, the channel 14 extends through the GISDS 10 and is configured to flow the fluid to a piston assembly 60. In the illustrated embodiment, the piston assembly 60 includes a chamber 62 (e.g., fluid-supporting chamber) and a piston 64 configured to move within a cylinder 65. In operation, a volume of fluid may flow into and be contained (e.g., isolated) within the chamber 62. Subsequently, the piston 64 may be retracted or withdrawn from the chamber 62, thereby increasing a volume of the chamber 62 and reducing a pressure within the chamber 62. In some embodiments, gas-in-solution within the fluid may undergo a phase transition to free gas within the increased volume and reduced pressure of the chamber 62. While examples provided herein relate to the piston assembly 60 having the piston 64 that moves within the cylinder 65 to facilitate discussion, it should be understood that any suitable actuator assembly may be utilized to monitor gas-in-solution (e.g., to isolate fluid within the chamber 62, increase the volume of the chamber 62 to reduce the pressure within the chamber 62). For example, the actuator assembly may include a diaphragm, balloon, or other resilient expandable member configured to adjust the volume of the chamber 62. It should be understood that multiple piston assemblies 60 may be provided along the channel 14 of the GISDS 10.

The GISDS 10 may include one or more sensors 85 (e.g., pressure sensors, temperature sensors, acoustic sensors, etc.) positioned along the channel 14 and/or within the piston assembly 60 to enable the one or more sensors 85 to monitor respective characteristics of the fluid indicative of the phase transition, free gas, and/or gas-in-solution. For example, in the illustrated embodiment, the GISDS 10 includes an acoustic transducer 66 (e.g., ultrasonic transducer) having a transceiver 82 configured to emit and to receive acoustic waves (e.g., ultrasonic waves). In operation, the transceiver 82 may emit acoustic waves into fluid contained within the chamber 62, the acoustic waves may be reflected from a surface 84 (e.g., opposed surface) of the piston 64, and the reflected acoustic waves may then be received by the transceiver 82. The transceiver 82 may be configured to generate a signal based on the received reflected acoustic waves. As shown, the GISDS 10 may include multiple pressure and/or temperature sensors 68 configured to monitor the pressure and/or the temperature of the fluid at various locations, which may be indicative of the phase transition, free gas, and/or gas-in-solution. As discussed in more detail below, the signals generated by the sensors 85 may be provided to a controller (e.g., electronic controller, such as a controller 96 having a processor 98 and a memory device 99) having electrical circuitry configured to process the signals to determine characteristics of the fluid.

Such characteristics may be utilized (e.g., by a controller or by an operator) to detect the presence or the absence of gas-in-solution and/or to determine appropriate outputs and/or actions. For example, certain characteristics (e.g., decrease in temperature at or downstream of the chamber 62, unexpected changes [i.e., unexpectedly small decrease] in pressure at the chamber 62 upon an increase in volume of the chamber 62, decrease in density of the fluid as evidenced by attenuation of acoustic waves within the chamber 62, or the like) may indicate a phase transition from gas-in-solution to free gas within the increased volume of the chamber 62 and/or the presence of free gas within the chamber 62, and thus, may indicate the presence of gas-in-solution in the fluid, such as due to an influx of formation fluid within drilling mud or a potential "kick" event. It should be understood that the sensors 85 shown in FIG. 2 are provided as examples and are not intended to be limiting, and that any of a variety of sensors 85 may be utilized within the GISDS 10, including the sensors 85 discussed above, as well as conductivity sensors configured to monitor the conductivity of the fluid, a capacitance sensors configured to monitor the capacitance of the fluid, chemical sensors (e.g., gas composition sensor or carbon dioxide sensor) configured to monitor the chemical levels (e.g., gas composition or carbon dioxide levels) within the fluid, spectrometry sensors (e.g., optical, infrared, radiation, mass, gamma-ray, nuclear magnetic resonance [NMR], and/or diffraction grating spectrometer assembly or sensor) configured to monitor absorption of light and/or energy by the fluid, viscosity sensors configured to monitor the viscosity of the fluid, density sensors configured to measure the density of the fluid, electrodes, and/or any other suitable sensors configured to monitor and to obtain signals indicative of fluid parameters, including a conductivity, a capacitance, a dielectric constant, a chemical level, a gas composition, a carbon dioxide level, an ultrasonic frequency, an ultrasonic velocity, absorption of light and/or energy, a density, a viscosity, a free gas content, an oil content, and/or a water content, for example. As discussed in more detail below, the signals from such sensors 85 may be processed by the controller to detect the presence or the absence of gas-in-solution. Such sensors 85 may be positioned to monitor fluid within the chamber 62 of the piston assembly 60 and/or at any suitable location along the channel 14 within the GISDS 10.

In the illustrated embodiment, the GISDS 10 includes a first isolation assembly 50 (e.g., double barrier isolation assembly) having two valves 52 (e.g., primary and secondary fail-closed valves) positioned proximate the first end 40 of the GISDS 10 and a second isolation assembly 54 (e.g., double barrier isolation assembly) having two valves 52 (e.g., primary and secondary fail-closed valves) positioned proximate the second end 42 of the GISDS 10. Each of the valves 52 may be configured to move between an open position to enable fluid flow across the valve 52 and a closed position to block fluid flow across the valve 52. The valves 52 may have any suitable configuration to adjust the flow of fluid through the GISDS 10 and/or to fail in the closed position to isolate the fluid (e.g., hydrocarbons) from the surrounding environment. For example, the valves 52 may be gate valves, ball valves, or the like. While the isolation assemblies 50, 54 in FIG. 2 include two valves 52, it should be understood that the isolation assemblies 50, 54 may include any suitable number (e.g., 1, 2, 3, 4, or more) of valves 52 and/or other barrier structures, such as plugs or rams, which are configured to enable and/or to block fluid flow.

The GISDS 10 may include any of a variety of valves in various locations. For example, in the illustrated embodiment, the GISDS 10 includes one-way valves 53 (e.g., check valves) to block fluid flow in the downstream direction. As shown, the GISDS 10 includes a piston isolation assembly 55 that includes a first valve 57 (e.g., fail-closed valve) positioned upstream of the piston assembly 60 and a second valve 59 (e.g., fail-closed valve) positioned downstream of the piston assembly 60. Each of the valves 57, 59 may be configured to move between an open position to enable fluid flow across the valve 57, 59 and a closed position to block fluid flow across the valve 57, 59. The valves 57, 59 may have any suitable configuration to adjust the flow of fluid through the GISDS 10 and/or to fail in the closed position. For example, the valves 57, 59 may be gate valves, ball valves, or the like. While the piston isolation assembly 55 in FIG. 2 include two valves 57, 59, it should be understood that the piston isolation assembly 55 may include any suitable number (e.g., 1, 2, 3, 4, or more) of valves and/or other barrier structures, such as plugs or rams, which are configured to enable and/or to block fluid flow. As shown, the piston assembly 60 and the one or more sensors 85 may be positioned between the isolation assemblies 50, 54, between the check valves 53, and/or between the valves 57, 59 of the piston isolation assembly 55 to monitor respective characteristics of the fluid as the fluid flows through the GISDS 10.

The illustrated embodiment also includes a filter 70 (e.g., debris filter, screen, mesh) configured to filter debris or particulate matter from the fluid, a flush system 71 having a flush line 72 (e.g., a fluid conduit or passageway) configured to provide a flush fluid (e.g., clean drilling mud, sea water, oil, diesel, detergent having various chemicals, control fluid, calibration fluid, or the like) into the channel 14 and/or the GISDS 10 and a flush line isolation assembly 73 having flush line valves 74 configured to adjust the flow of the flush fluid, and a pump 76 (e.g., a flow control device, a controllable or adjustable flow device, a variable measured circulating flow device, or an adjustable controlled volume circulation pump) configured to adjust the flow rate of the fluid through the GISDS 10. As shown, the filter 70 is positioned upstream from the piston assembly 60 and the one or more sensors 85 (e.g., between the first isolation assembly 50 and the piston assembly 60 and the one or more sensors 85) to remove debris from the fluid prior to monitoring the characteristics of the fluid in the chamber 62 of the piston assembly 60 and/or using the one or more sensors 85. In some embodiments, the GISDS 10 may include multiple filters 70 or a multi-stage filter.

In the illustrated embodiment, the pump 76 is positioned downstream of the piston assembly 60 and the one or more sensors 85 (e.g., between the piston assembly 60 and the second isolation assembly 54). Such a configuration enables the pump 76 to control a flow rate of the fluid through the GISDS 10 without shearing and/or mixing the fluid prior to monitoring the fluid within the chamber 62 of the piston assembly 60 and/or using the one or more sensors 85. The pump 76 may be hydraulically, pneumatically, magnetically, or electrically actuated and may have any suitable form (e.g., rotary pump, reciprocating pump, or centrifugal pump) for circulating and/or adjusting the flow rate of the fluid through the GISDS 10. For example, the pump 76 may include a piston, rotating plates, screw, vane, or the like to pump the fluid through the channel 14.

Additionally or alternatively, in some embodiments, other types of flow control devices (e.g., choke valves, flow restrictors, controllable or adjustable flow devices, and/or variable measured circulating flow devices) may be provided as part of the GISDS 10 and/or positioned within the housing 26, or they may be positioned at any suitable location along the conduit 12 and/or the channel 14. For example, in some embodiments, a flow restrictor 77 (e.g., a section having a reduced cross-sectional flow area, a throat, a venturi, or the like) may be provided between the first and second portions 20, 24 of the conduit 12 to restrict flow through the conduit 12, thereby facilitating flow of fluid from the conduit 12 into the channel 14. Additionally or alternatively, a throttling valve 79 (e.g., choke valve) may be positioned downstream of the piston assembly 60 and the one or more sensors 85 (e.g., between the piston assembly 60 and the second isolation assembly 54 proximate to or at the location of the pump 76) to throttle fluid flow through the channel 14. In some embodiments, the choke valve 79 may be utilized instead of the pump 76 to control the flow rate of the fluid through the channel 14, and a flow meter 81 may be utilized to monitor the flow rate of the fluid through the channel 14. The flow restrictor 77, the throttling valve 79, and the flow meter 81 are shown in dashed lines in FIG. 2 to facilitate discussion of these features that may be utilized in the GISDS 10, possibly instead of the pump 76, for example.

When the flush line valves 74 are in an open position, the flush line valves 74 may enable the flush fluid to flow through the flush line 72 into the channel 14 and/or other suitable region of the GISDS 10. In operation, the flush fluid may be utilized to flush or to clear debris trapped by the debris filter 70 and/or to flush the channel 14. As discussed in more detail below, in certain embodiments, the flush fluid may be utilized in various processes to test the isolation assemblies 50, 54, test the sensors 85, and/or to calibrate the sensors 85. Although the illustrated embodiment includes two flush line valves 74 to create a double isolation barrier, it should be understood that any suitable number (e.g., 1, 2, 3, 4, or more) of flush line valves 74 may be provided to control flow of the flush fluid and/or to isolate the channel 14 from the environment. In some embodiments, a heat source 75 (e.g., heat exchanger, electrical heater, coils, or the like) may be provided within the GISDS 10 to block (e.g., prevent) hydrate formation and/or to facilitate the flushing process.

The channel 14 through the GISDS 10 may have any suitable geometry to direct the fluid from the first end 40 to the second end 42 of the GISDS 10 and to enable fluid flow into the chamber 62 of the piston assembly 60 and monitoring by the sensors 85. In some embodiments, the channel 14 may have a circular cross-sectional shape and/or a rectangular cross-sectional shape. In some embodiments, the channel 14 may have a width or a diameter 80 that defines a cross-sectional flow area. In some embodiments, the width or the diameter 80 may be equal to or less than approximately 1.5, 2, 2.5, or 3 centimeters (cm). In some embodiments, the width or the diameter 80 may be between approximately 1 to 5, 1.5 to 3, or 2 to 2.5 centimeters. In some embodiments, the width or the diameter 80 of the channel 14 may be equal to or less than approximately 3, 5, 10, 15, 20, or 25 percent of a diameter of the conduit 12. In some embodiments, the width or the diameter 80 (or the corresponding cross-sectional flow area) may be generally constant between the first and second ends 40, 42 of the GISDS 10. In other embodiments, the width or the diameter 80 may vary between the first and second ends 40, 42 of the GISDS 10 (e.g., the channel 14 may have a first diameter 80 at a first portion and a second diameter 80 at a second portion).

As discussed above, the GISDS 10 may include the controller 96 having the processor 98 and the memory device 99. In certain embodiments, the controller 96 may be configured to receive and to process the signals from the sensors 85 and/or to provide control signals to certain components of the GISDS 10, for example. In particular, the controller 96 may provide control signals (e.g., to various valves) to isolate fluid within the chamber 62, to actuate the piston 64, and to operate the sensors 85. The controller 96 may be configured to receive data indicative of the position of the piston 64, and thus, the volume of the chamber 62 (e.g., a change in volume of the chamber 62), which may be utilized to identify gas-in-solution (e.g., a resultant or an indicator of gas-in-solution) and/or free gas. The controller 96 may also be configured to receive signals from the sensors 85 and to process the signals (e.g., using one or more algorithms) to determine characteristics of the fluid, such as the pressure, the temperature, and/or the velocity and/or attenuation of acoustic waves, and thereby identify gas-in-solution of the fluid (e.g., the resultant or the indicator of gas-in-solution, such as changes in pressure, changes in temperature, and/or bubbles or free gas within the chamber) and/or free gas within the fluid. In some embodiments, the controller 96 may detect the absence or the presence of gas-in-solution. In some embodiments, the controller 96 may be configured to determine an amount or ratio of gas-in-solution (e.g., estimate or quantify the gas-in-solution using one or more algorithms). In some embodiments, the controller 96 may be configured to calculate a bubble point of the fluid based on the temperature and the pressure at which bubbles (e.g., gas) are formed and/or detected in the fluid.

In some embodiments, the controller 96 may compare the sensor data obtained by one or more sensors 85 within one GISDS 10 at different times to identify changes in the fluid over time. Such analysis may be particularly useful in monitoring changes in fluids produced by a well over time, for example. Additionally or alternatively, in some embodiments, the controller 96 may compare sensor data obtained by one or more sensors 85 of multiple different GISDS 10 positioned at different locations of the drilling system and/or the production system at different times or in real time or at the same time to identify changes in the fluid during the drilling and/or production process. Such analysis may be particularly useful in monitoring changes in supplied fluids during drilling processes, for example.

In some embodiments, the controller 96 may be configured to provide an output (e.g., visual or audible output or an instruction or control signal) based on the sensor data. For example, the controller 96 may be configured to provide a visual or audible output that indicates the presence or absence of gas-in-solution, the amount of gas-in-solution, a trend or a change in the gas-in-solution over time, a rate of change of the gas-in-solution over time, a change in the gas-in-solution as compared to a predetermined acceptable range (e.g., upper threshold, lower threshold, or both) and/or baseline data (e.g., historical data, known data, modeled data, sensor data obtained by the same GISDS 10 at a previous time, sensor data obtained by one or more upstream GISDS 10 or one or more other GISDS 10 within the drilling and/or production system at a previous time or at the same time, or the like). It should be understood that the controller 96 may additionally or alternatively be configured to provide an output indicative of various other characteristics (e.g., pressure, temperature, density, or the like), as well as changes in such characteristics, in a similar manner.

In some embodiments, the controller 96 may be configured to initiate an alarm (e.g., a visual or audible alarm, such as a textual warning message or beep) if gas-in-solution is detected (e.g., in drilling mud) and/or if the amount, change, and/or rates of change of gas-in-solution exceed or differ from predetermined acceptable ranges and/or baseline data (e.g., in production fluids). In some embodiments, such as in drilling systems, the controller 96 may be configured to initiate the alarm upon detection of any gas-in-solution in drilling fluids. In some embodiments, the controller 96 may be configured to provide a prompt, such as instructions to perform maintenance or repair operations, conduct further monitoring using certain GISDS 10 and/or certain sensors 85 within certain GISDS 10, flush the channel 14, to close the well, actuate a control device (e.g., a valve or the diverter), or the like, based on detected gas-in-solution and/or other monitored characteristics. For example, if the controller 96 detects (e.g., based on signals from the sensors 85 and using one or more algorithms) the presence of gas-in-solution using one GISDS 10 downstream of the wellbore (e.g., indicating a sudden influx of formation fluid within drilling mud in the conduit 12, commonly known as a "kick,") the controller 96 may provide an alarm and/or instructions to actuate the diverter to divert fluid from the platform and/or to the BOP to seal the annulus to control fluid pressure in the wellbore.

In some embodiments, the controller 96 may be configured to provide control signals to various components of the GISDS 10 and/or the drilling and/or production system based on detected gas-in-solution and/or monitored characteristics in a similar manner. For example, in some embodiments, the controller 96 may provide control signals to automatically repeat measurements using one or more sensors 85 of the GISDS 10, flush the channel 14, activate certain sensors 85 within one or more other GISDS 10 within the drilling and/or production system, close the BOP assembly, actuate the diverter, or the like. In some embodiments, the controller 96 may be configured to initiate the alarm, provide the prompt, and/or provide the control signals if the gas-in-solution and/or sensor data 85 from one or more GISDS 10 varies from a predetermined acceptable range and/or baseline data by more than 1, 2, 3, 4, 5, 6, 7, 8, 9, 10, 15, or 20 percent and/or if the gas-in-solution, characteristic, trend, change, and/or rate of change indicates a kick event or other event. In some embodiments, the controller 96 may be configured to receive respective signals from multiple GISDS 10 distributed about the drilling and/or production system, analyze the signals together (e.g., using one or more algorithms) to determine whether the signals indicate gas-in-solution or otherwise indicate atypical fluid composition or atypical fluid changes or rates of change, and to provide the information, alarm, prompt, and/or control signals in the manner set forth above.

As noted above, in certain embodiments, the controller 96 may be configured to control the various components of the GISDS 10, including the sensors 85, the piston 64, the valves 52, 74, 57, 59 and/or the pump 76. For example, the controller 96 may be configured to provide a control signal to the valves 52, 74 to cause the valves 52, 74 to move between an open position and a closed position, a control signal to a valve of the piston assembly 60 to provide control fluid to drive the piston 64 within the cylinder 65, a control signal to the acoustic transducer 66 to cause the transceiver 82 of the acoustic transducer 66 to emit an acoustic wave, and/or a control signal to control the pump 76 to adjust the flow rate of the fluid through the channel 14. In some embodiments, the controller 96 may be configured to activate or to operate the components of the GISDS 10 in a predetermined sequence or according to a predetermined program. Certain sensors 85 may provide accurate and/or reliable measurements of the fluid under particular conditions (e.g., flow rate, turbulent flow, laminar flow, stationary or stagnant, pressure, temperature, or the like). Thus, in some embodiments, the processor 98 may control the pump 76 to adjust the flow rate to a first flow rate that is appropriate for a first sensor 85 and may then activate the first sensor 85 to measure a respective characteristic of the fluid. Subsequently, the processor 98 may control the pump 76 to adjust the flow rate to a second flow rate, different from the first flow rate and that is appropriate for a second sensor 85, and the processor may then activate the second sensor 85 to measure a respective characteristic of the fluid. The controller 96 may be configured to operate the valves 52, 74, 57, 59 the sensors 85, the piston 64, and/or the pump 76 periodically (e.g., at predetermined intervals) during drilling and/or production processes and/or in response to a control signal generated in response to a user input, detected gas-in-solution, measured characteristics, or the like.

The controller 96 may be located at any suitable location to enable the controller 96 to receive signals from the sensors 85 of the GISDS 10 and/or to control components of the GISDS 10. For example, the controller 96 may be positioned within the housing 26, within a separate support structure coupled to the housing 26, and/or at a location remote from the housing 26 (e.g., surface location). As discussed in more detail below, in certain embodiments, the controller 96 may be part of a distributed controller or control system with one or more controllers (e.g., electronic controllers with processors, memory, and instructions) distributed about the drilling system or the production system and in communication with one another to receive and/or to process the signals from one or more GISDS 10, to provide an output, and/or to control the components of the GISDS 10. For example, as discussed in more detail below, one controller (e.g., the controller 96) may be positioned within the housing 26 of the GISDS 10 and may be configured to receive and to process the signals from the sensors 85 of the GISDS 10 and another controller may be positioned in a remote or topside base station that is configured to determine and/or to provide the appropriate output (e.g., via a display for visualization by an operator). In some embodiments, one controller (e.g., the controller 96) may be configured to control the components of the GISDS 10 and to provide the signals generated by the sensors 85 to another controller, which may include a processor configured to aggregate data or signals from the sensors 85 of multiple different GISDS 10 and to provide the appropriate output. Thus, the controller 96 may not further process the raw data obtained by the sensors 85, but rather the controller 96 may store the raw data (e.g., in the memory device 99) and/or facilitate communication of the data to another controller (e.g., a controller of a remote base station) for further processing. Thus, the controller 96 may carry out some or all of the processing steps with respect to the signals obtained from the sensors 85 of the GISDS 10.

It should be understood that any of the controllers disclosed herein (e.g., the controller 96) may include respective a processor (e.g., the processor 98), a respective memory device (e.g., the memory device 99), and/or one or more storage devices and/or other suitable components. Furthermore, the processors disclosed herein may be used to execute software, such as software for processing signals and/or controlling the components of the GISDS 10. Moreover, the processors may include multiple microprocessors, one or more "general-purpose" microprocessors, one or more special-purpose microprocessors, and/or one or more application specific integrated circuits (ASICS), or some combination thereof. For example, the processors may include one or more reduced instruction set (RISC) or complex instruction set (CISC) processors. The memory devices disclosed herein may include a volatile memory, such as random access memory (RAM), and/or a nonvolatile memory, such as ROM. The memory devices may store a variety of information and may be used for various purposes. For example, the memory devices may store processor-executable instructions (e.g., firmware or software) for the processors to execute, such as instructions for processing signals received from the sensors and/or controlling the components of the GISDS 10. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., acceptable ranges, baseline data, sensor data, desired flow rates or pump parameters, or the like), instructions (e.g., software or firmware for controlling the components of the GISDS 10, or the like), and any other suitable data.

Advantageously, the GISDS 10 may enable real-time fluid monitoring under controlled conditions (e.g., flow rate, pressure, temperature, or the like) within the chamber 62 and/or the channel 14 and/or may provide a configuration that enables the sensors 85 to obtain accurate and/or reliable measurements. Additionally, the GISDS 10 may monitor the fluid regardless of fluid flow within the conduit 12 (e.g., regardless of whether the fluid flow within the conduit 12 is turbulent, stationary or stagnant, or the like) and/or regardless of whether drilling equipment is positioned within the conduit 12, for example.

It should be understood that the GISDS 10 may include some or all of the components shown in FIG. 2 and/or that other components may be added. Furthermore, such components may have any suitable arrangement (e.g., order, spacing, relative positioning, or the like) within the GISDS 10. Additionally, the components of the GISDS 10 may be controlled by any suitable control system having one or more controllers, such as the controller 96. As used herein, the terms upstream and downstream are defined with respect to a flow path of the fluid. For example, in the illustrated embodiment, the first end 40 of the GISDS 10 is upstream from the second end 42 of the GISDS 10, because the fluid flows from the first end 40 toward the second end 42.

Figure 3:
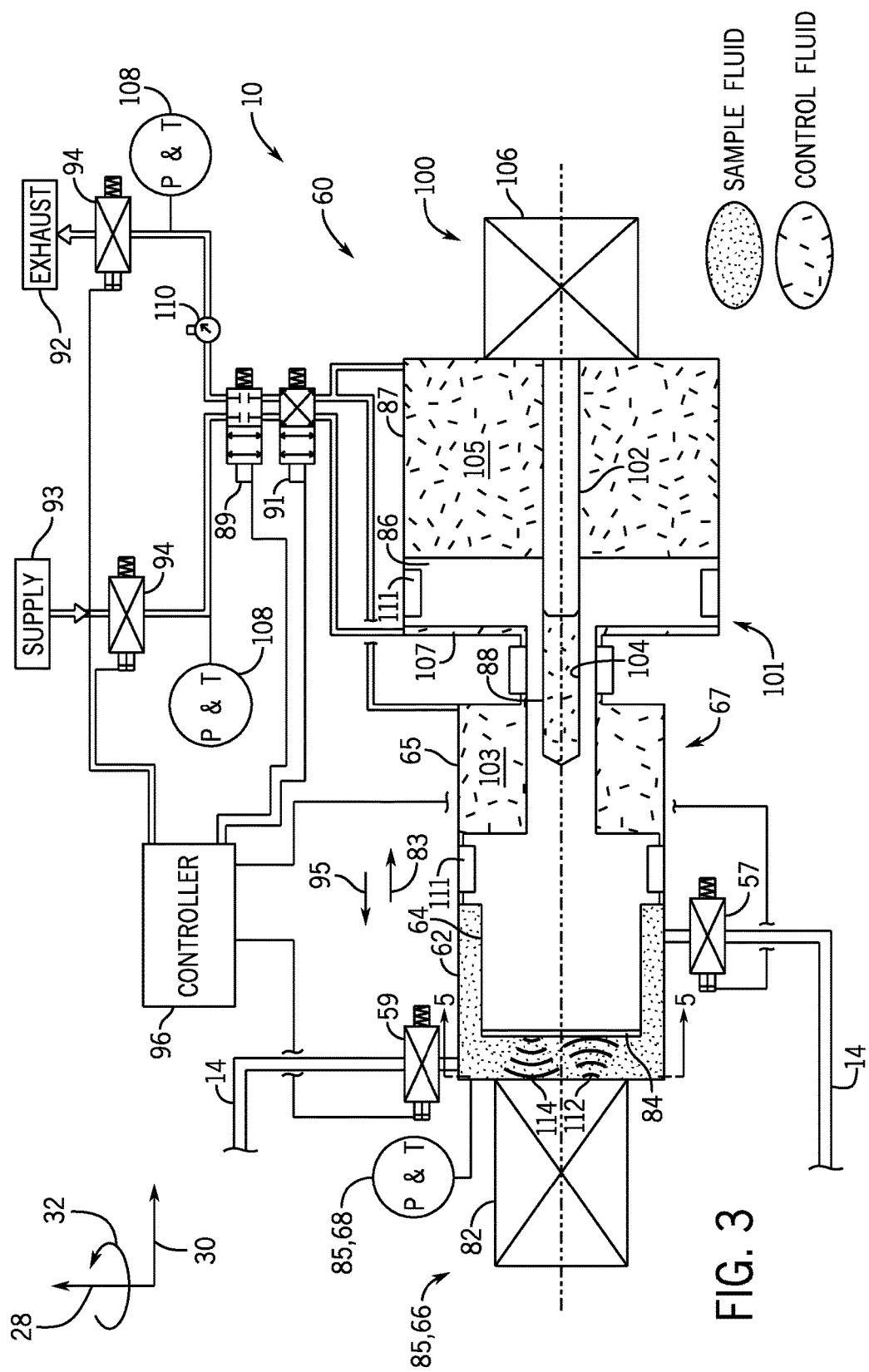
FIG. 3 is a schematic diagram of a piston assembly that may be utilized within the GISDS, wherein a piston of the piston assembly is in a first position, in accordance with an embodiment of the present disclosure.
Figure 4:
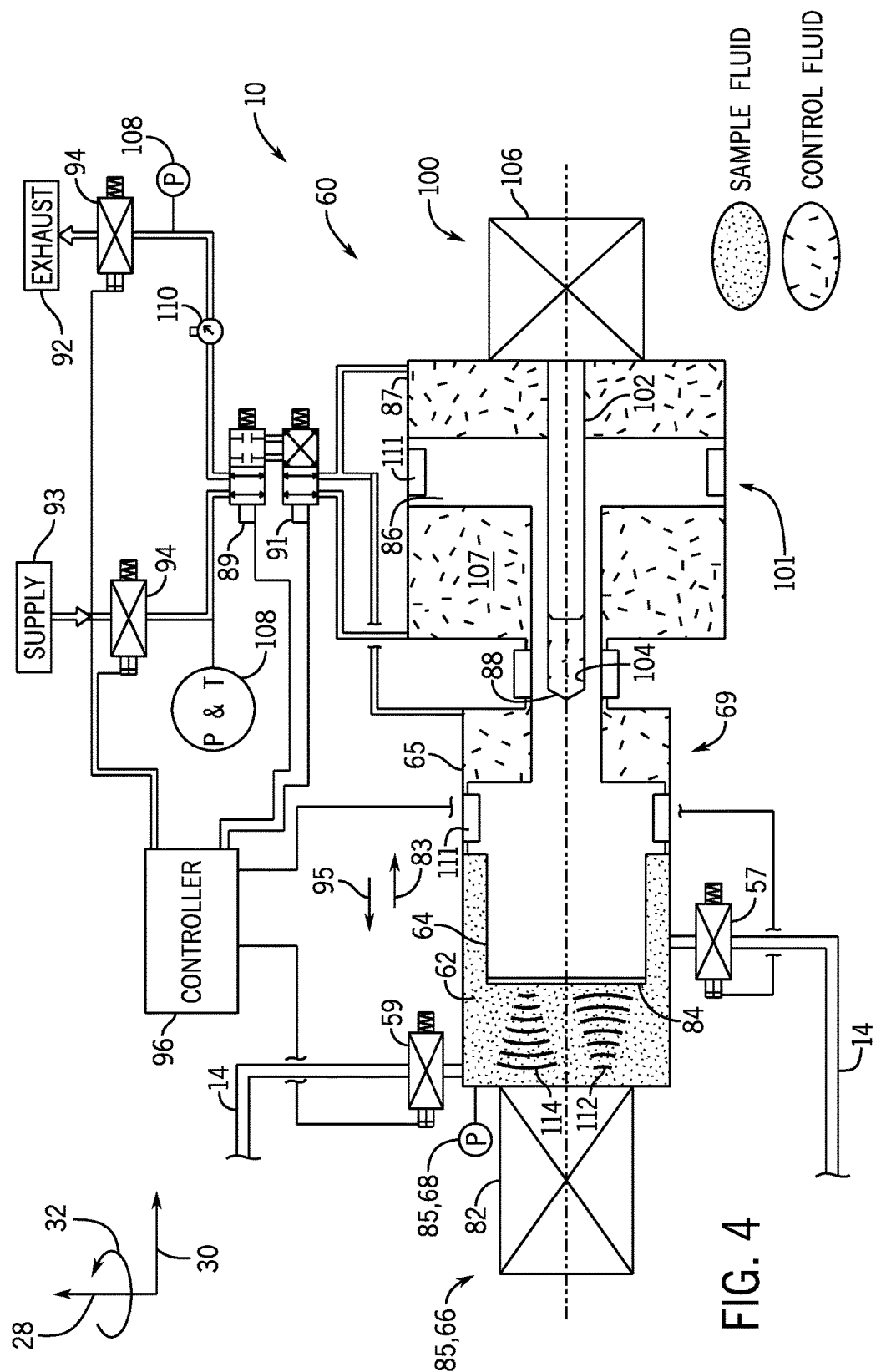
FIG. 4 is a schematic diagram of the piston assembly of FIG. 3, wherein the piston of the piston assembly is in a second position, in accordance with an embodiment of the present disclosure.

FIGS. 3 and 4 are schematic diagrams of an embodiment of the piston assembly 60 that may be utilized within the GISDS 10. As discussed in more detail below, the piston 64 of the piston assembly 60 may be maintained in a first position 67 (e.g., extended position) illustrated in FIG. 3 until a volume of fluid is received and contained (e.g., trapped or isolated) within the chamber 62. Once the volume of fluid is contained within the chamber 62, the piston 64 may be controlled to move to a second position 69 (e.g., retracted position) illustrated in FIG. 4 to increase a volume and to decrease a pressure of the chamber 62, which may facilitate transition of gas-in-solution to free gas within the chamber 62 and/or otherwise enable monitoring of the fluid under reduced pressure.

With the foregoing in mind, in operation, fluid (e.g., from the conduit 12) flows through the channel 14 of the GISDS 10 (e.g., via operation of the pump 76 and various valves 52, 57, 59) into the chamber 62. To facilitate monitoring gas-in-solution, a volume of fluid may be contained within the chamber 62 of the piston assembly 60, such as by controlling the first valve 57 and the second valve 59 to closed positions to block fluid flow across the valves 57, 59. Once a fixed volume of fluid is contained within the chamber 62 (e.g., after closing the valves 57, 59), a volume of the chamber 62 may be adjusted (e.g., increased) to change (e.g., decrease) the pressure within the chamber 62. As noted above, in some embodiments, the volume of the chamber 62 may be increased by driving the piston 64 in the direction of arrow 83 to the second position 69, shown in FIG. 4. In some embodiments, the volume of the chamber 62 may be increased by an amount equal to or greater than approximately 5, 10, 20, 30, 40, 50, 60, 70, or 80 percent. In some embodiments, the volume of the chamber 62 may be increased until the pressure decreases by an amount equal to or greater than approximately 5, 10, 20, 30, 40, 50, 60, 70, 80, 90, or 95 percent. In some embodiments, the volume of the chamber 62 may be increased until the pressure within the chamber 62 is equal to or less than approximately 1, 10, 100, 500, or 1000 Megapascal (MPa).

The piston 64 may be driven via any suitable hydraulic, pneumatic, or electronic drive system. In the illustrated embodiment, the piston assembly 60 comprises a double piston assembly 101 (e.g., intensifier piston assembly) having the piston 64 configured to move within the cylinder 65 and a secondary piston 86 configured to move within a secondary cylinder 87. As shown, the piston 64 and the secondary piston 86 are coupled to one another via a connecting rod 88.

In operation, the controller 96 may be configured to provide control signals to valves, such as a first valve 89 (e.g., selector valve or pilot valve) and a second valve 91 (e.g., selector valve or pilot valve), to drive the piston 64 between the first position 67 and the second position 69. To drive the piston 64 to the first position 67, as shown in FIG. 3, the first valve 89 enables fluid flow across the first valve 89, and the second valve 91 enables fluid flow from a fluid supply 93 (e.g., a control fluid supply) to a seal spaced 103 within the cylinder 65 and a sealed space 105 within the secondary cylinder 87 to drive the pistons 64, 86 in the direction of arrow 95. At the same time, fluid is vented from a sealed space 107 to the exhaust outlet 92. In some embodiments, the first valve 89 may then be adjusted to another position (e.g., the illustrated position) in which the first valve 89 blocks fluid flow across the first valve 89 in order to maintain the first position 67. To drive the piston 64 to the second position 69, as shown in FIG. 4, the first valve 89 enables fluid flow across the first valve 89, and the second valve 91 enables fluid flow from the fluid supply 93 to a sealed spaced 107 within the second cylinder 87 to drive the pistons 64, 86 in the direction of arrow 83. The second valve 91 also enables fluid flow from the cylinders 65, 87 to an exhaust outlet 92 as the pistons 64, 86 move in the direction of arrow 83. In some embodiments, the first valve 89 may then be adjusted to another position (e.g., the illustrated position) in which the first valve 89 blocks fluid flow across the first valve 89 in order to maintain the second position 69.

In some embodiments, the double piston assembly 101 may be moved incrementally in the direction of arrow 83. For example, the double piston assembly 101 may be moved from the first position 67 to a first intermediate position toward the second position 69, and the acoustic transducer 66 and/or other sensors 85 may be operated to obtain data while the double piston assembly 101 is in the first intermediate position. If no gas-in-solution is detected, the double piston assembly 101 may then be moved to a second intermediate position toward the second position 69, and the acoustic transducer 66 and/or other sensors 85 may be operated to obtain data while the double piston assembly 101 is in the second intermediate position. This process may be carried out until the double piston assembly 101 reaches the second position 69 and/or until the volume of the chamber 62 is increased to a point at which the absence of gas-in-solution can be confirmed and/or the amount of gas-in-solution can be reliably determined. In some embodiments, movement of the double piston assembly 101 may be blocked or stopped once gas-in-solution is detected and/or once the amount of gas-in-solution is determined. After completion of the monitoring of the fluid in the chamber 62, the valves 89, 91 may be controlled to drive the double piston assembly 101 back to the first position 67 to compress the fluid and/or the valves 57, 59 may be opened to facilitate fluid flow out of the chamber 62 and to return the fluid toward the conduit 12. As shown, the valves 89, 91 may be fail-closed valves configured to fail in a closed position that blocks fluid flow across the valves 89, 91.

As shown, the piston assembly 60 includes shut-off valves 94 (e.g., isolation valves) that control fluid flow from the fluid supply 93 and to the exhaust outlet 92. The shut-off valves 94 may be configured to move to a position to block the fluid, and any hydrocarbons contained therein, from flowing to the supply 93 and/or the exhaust outlet 92 in the event that seals 111 (e.g., annular seals) of the piston assembly 60 fail, for example. As shown, the piston assembly 60 includes pressure and/or temperature sensors 108 and/or a pressure regulator 110. As shown, the piston assembly 60 includes a position monitoring system 100 that is configured to monitor a position of the double piston assembly 101. For example, in the illustrated embodiment, the position monitoring system 100 includes a linear variable differential transformer (LVDT) sensor having a rod 102 that fits within a recess 104 of the secondary piston 86 and circuitry 106 (e.g., processing circuitry) configured to output a signal indicative of the position of the double piston assembly 101, although any suitable sensor configured to monitor the position of the piston 64 may be utilized within the piston assembly 60 (e.g., non-contact, magnetic, inductive, capacitive, acoustic, optical, proximity switch, encoders, or the like). The position of the piston assembly 101 may provide an indication of the volume of the chamber 62, which may be utilized by the controller 96 (e.g., in one or more algorithms) in combination with other data and inputs to detect gas-in-solution, to control the pistons 64, 86, or the like.

Before, during, and/or after adjustment of the volume of the chamber 62 (e.g., by moving the double piston assembly 101), the transceiver 82 of the acoustic transducer 66 may emit acoustic waves 112 (e.g., ultrasonic waves) into the chamber 62. The acoustic waves may be reflected by the surface 84 of the piston 64, and the reflected acoustic waves 114 may be detected by the acoustic transducer 66. The acoustic transducer 66 may generate a signal based on the reflected acoustic waves 114, and the signal may be processed to detect gas-in-solution in the fluid. For example, in some embodiments, some or all of the gas-in-solution may come of out of solution as the volume of the chamber 62 expands, and the free gas may then be detected based on characteristics of the reflected acoustic waves, such as velocity, attenuation, or the like. For example, the acoustic waves may be attenuated more by a fluid that does not contain gas-in-solution as compared to a fluid that contains gas-in-solution (e.g., due to the transition to and presence of free gas). One or more pressure and/or temperature sensors 68 may be positioned to monitor the pressure and/or the temperature within the chamber 62, which may be indicative of the phase transition from gas-in-solution to free gas. For example, for a given increase in the volume of the chamber 62, the pressure within the chamber 62 may decrease a first, greater amount (e.g., by an expected amount) if the fluid does not contain any gas-in-solution, while the pressure within the chamber 62 may decrease a second, lesser amount if the fluid contains gas-in-solution (e.g., due to the transition to free gas). For example, a decrease in temperature after increasing the volume of the chamber 62 may indicate the phase transition to free gas and the presence of gas-in-solution.

The piston assembly 60 is provided as an example to facilitate discussion. It should be understood that the transceiver 82 may be positioned at any suitable location about the piston assembly 60 that enables the transceiver 82 to emit acoustic waves into the fluid within the chamber 62, and that the acoustic waves may be reflected by any suitable surface (e.g., a wall of the chamber 62 or a radially-outer wall of the piston 64), and/or the reflected acoustic waves may be reflected toward and detected by a receiver separate from the transceiver 82.

Figure 5:
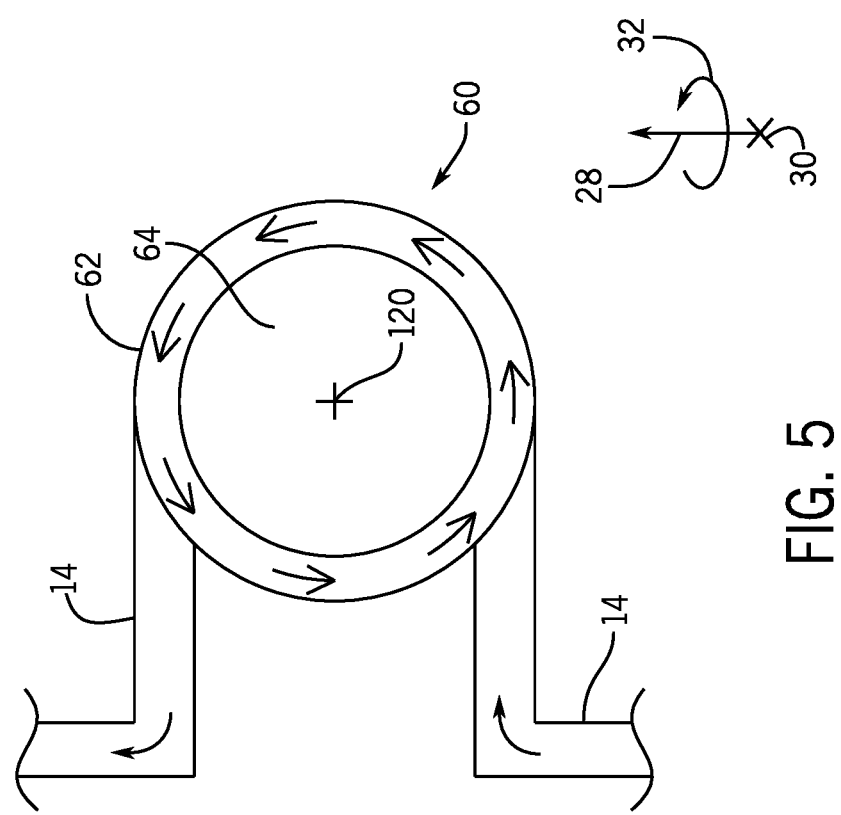
FIG. 5 is a schematic diagram of a fluid flow within a chamber of the piston assembly of FIG. 3, taken within lines 5-5 of FIG. 3, in accordance with an embodiment of the present disclosure.

FIG. 5 is a schematic diagram of a fluid flow within the chamber 62 of the piston assembly 60 taken within lines 5-5 of FIG. 3, in accordance with an embodiment of the present disclosure. As shown, the channel 14 is positioned to flow the fluid along a flow path that is tangential (e.g., offset from a longitudinal axis 120 of the piston 64 in the direction 28) to the piston 64 within the chamber 62. Such a configuration facilitates circumferential flow about the piston 64 (e.g., between the piston 64 and the chamber 62) and facilitates distribution of the fluid throughout the chamber 62, which may in turn facilitate monitoring and/or accurate detection of characteristics of the fluid.

Figure 6:
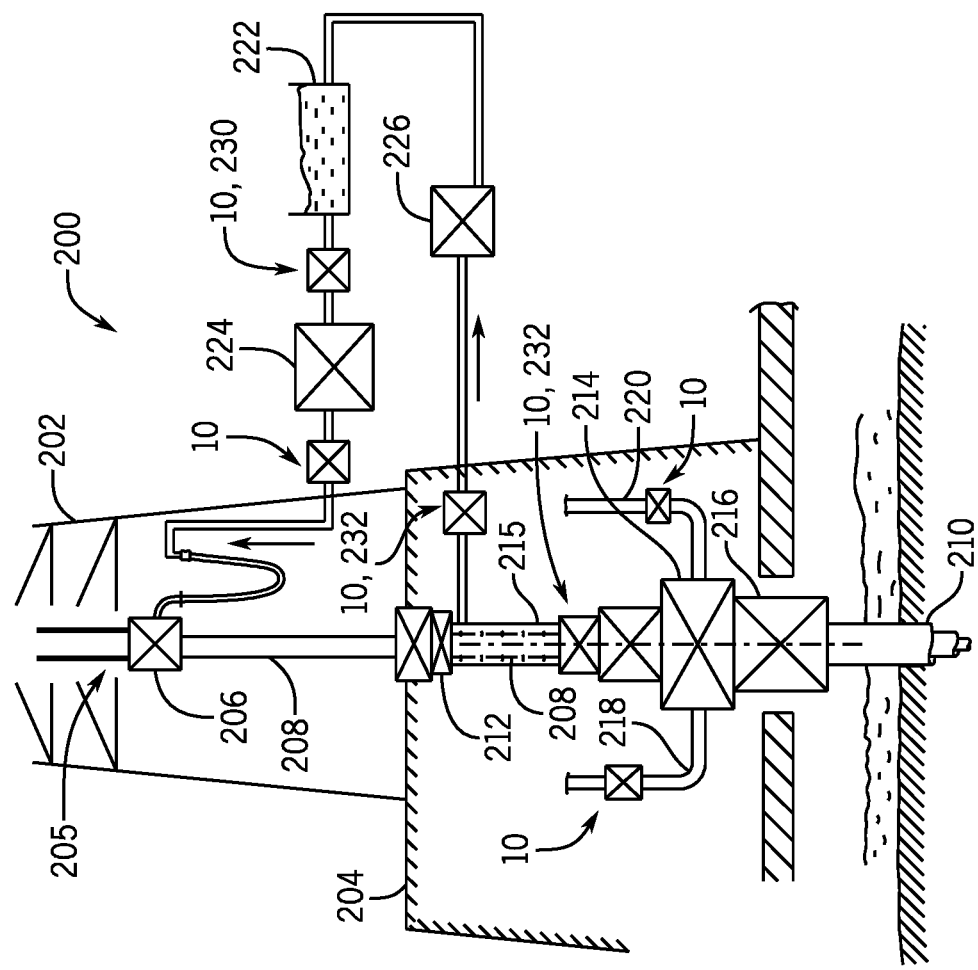
FIG. 6 is a schematic diagram showing multiple GISDS positioned at various locations within a surface drilling system, in accordance with an embodiment of the present disclosure.

FIGS. 6-11 are schematic elevation diagrams showing the GISDS 10 positioned at various locations within drilling and/or productions systems. In particular, FIG. 6 is a schematic diagram showing multiple GISDS 10 positioned at various locations within a surface drilling system 200, in accordance with an embodiment of the present disclosure. As shown, the system 200 includes a mast 202 (e.g., derrick) positioned on a drill floor 204. The system 200 may include a hoisting system 205 having a kelly or top drive 206. The hoisting system 205 may be used to raise and to lower drilling equipment relative to the drill floor 204, and the top drive 206 may be used to support and/or to rotate the drilling equipment. As shown, a drill pipe 208 (e.g., drill string) is suspended from the top drive 206 and extends through the drill floor 204 into a wellbore 210. The system 200 may include various other components, such as a diverter 212 (or rotating control device in a managed pressure drilling system), a blowout preventer (BOP) assembly 214 having one or more ram and/or annular BOPs, a bell nipple 215 (e.g., annular pipe), and a wellhead 216. As shown, a choke line 218 and a kill line 220 extend from the BOP assembly 214 to direct fluid to a fluid processing system at the drill floor 204 or other location. In some embodiments, the system 200 may be configured to managed pressure drilling (MPD) operations.

During drilling operations, the top drive 206 may rotate the drill pipe 108 to facilitate drilling the wellbore 210 and drilling mud may be pumped from a mud tank 222 (e.g., storage tank) through the drill pipe 208 toward the wellbore 210 via a mud pump 224. The drilling mud may return toward the drill floor 204 via an annular space between the drill pipe 208 and the bell nipple 215. The diverter 212 may divert the drilling mud toward a mud processing device 226 (e.g., shale shaker), which may separate debris or particulate matter from the drilling mud prior to returning the drilling mud to the mud tank 222.

As shown, respective GISDS 10 may be positioned upstream of the drill pipe 208, such as between the mud tank 222 and the mud pump 224 and/or between the mud pump 224 and the drill pipe 208, axially above the BOP assembly 214 (e.g., between the BOP assembly 214 and the diverter 212), along the choke line 218, along the kill line 220, and/or between the bell nipple 215 and the mud processing device 226, for example. In certain embodiments, the sensor data or characteristics of the fluid (e.g., drilling mud) obtained by the various GISDS 10 may be compared to one another, to predetermined acceptable ranges, and/or to baseline data (e.g., by the controller 96). For example, a first GISDS 10, 230 (e.g., an upstream GISDS) may be positioned to obtain a first set of characteristics (e.g., baseline data) of the fluid prior to injection into the drill pipe 208 and/or the wellbore 110. A second GISDS 10, 232 (e.g., a downstream GISDS or return GISDS) may be positioned to obtain a second set of characteristics from the annular as the fluid flows around the drill pipe 208 and/or during or after return of the fluid to the surface.

In certain embodiments, the characteristics of the fluid measured by each GISDS 10 may be compared to the first set of characteristics and/or to characteristics measured by other GISDS 10 to facilitate detection of gas-in-solution and/or to detect unacceptable changes (e.g., more than 1, 2, 3, 4, 5, 6, 7, 8, 9, 10, 15, or 20 percent) and/or to detect unacceptable rates of changes in the characteristics of the fluid during the drilling process. For example, comparison of the second set of characteristics to the first set of characteristics may provide an indication of the presence of gas-in-solution, free gas, increased oil or gas content, or the like, which may prompt a control system (e.g., having the controller 96) to provide an appropriate output, such as an alarm, a prompt, a control signal to actuate valves to block fluid flow, or the like.

Figure 7:
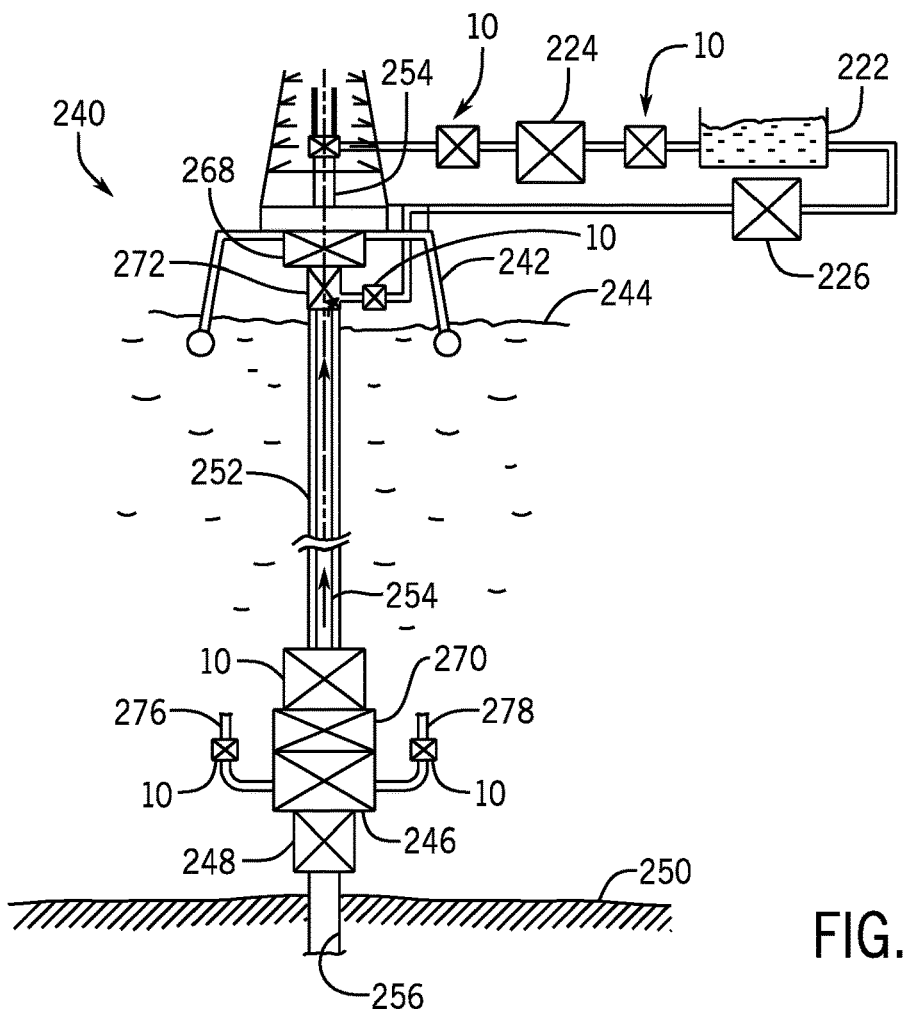
FIG. 7 is a schematic diagram showing multiple GISDS positioned at various locations within a subsea drilling system, in accordance with an embodiment of the present disclosure.

FIG. 7 is a schematic elevation diagram showing multiple GISDS 10 positioned at various locations within a subsea drilling system 240, in accordance with an embodiment of the present disclosure. As shown, the system 240 includes an offshore vessel or platform 242 at a sea surface 244. A BOP stack assembly 246 is mounted to a wellhead 248 at a sea floor 250, and a tubular drilling riser 252 extends from the platform 242 to the BOP stack assembly 246. Downhole operations are carried out by a drill pipe 254 (e.g., drill string) that extends from the platform 242, through the riser 252, through the BOP stack assembly 246, and into a wellbore 256. The system 240 may include various other components, such as a diverter 268, a lower marine riser package 270 (LMRP) having one or more annular BOPs, and a bell nipple 272 (e.g., annular pipe). As shown, a choke line 276 and a kill line 278 extend from the BOP assembly 246 to direct fluid to a fluid processing system at the platform 242 or other location.

During drilling operations, the drill pipe 254 may rotate to drill the wellbore 256 and drilling mud may be pumped from the mud tank 222 through the drill pipe 254 toward the wellbore 256 via the mud pump 224. The drilling mud may return toward the platform 242 via an annular space between the drill pipe 254 and the riser 252. The diverter 268 may divert the drilling mud toward a mud processing device 226 at the platform 242 or other location, which may separate debris or particulate matter from the drilling mud prior to returning the drilling mud to the mud tank 222.

As shown, respective GISDS 10 may be positioned upstream of the drill pipe 254, such as between the mud tank 222 and the mud pump 224 and/or between the mud pump 224 and the drill pipe 254, axially above the BOP assembly 246 and the LMRP 270 (e.g., between the LMRP 270 and the diverter 268), along the choke line 276, along the kill line 278, and/or between the diverter 268/bell nipple 272 and the mud processing device 226, for example. In certain embodiments, the sensor data or characteristics of the fluid (e.g., drilling mud) obtained by the various GISDS 10 may be compared to predetermined acceptable ranges and/or baseline data to detect gas-in-solution, provide an output, or the like, as discussed above with respect to FIGS. 2-6, for example. In certain embodiments, control lines (e.g., umbilicals) may extend from the GISDS 10 positioned at subsea locations to the surface to enable exchange of signals between surface control systems and the GISDS 10.

Figure 8:
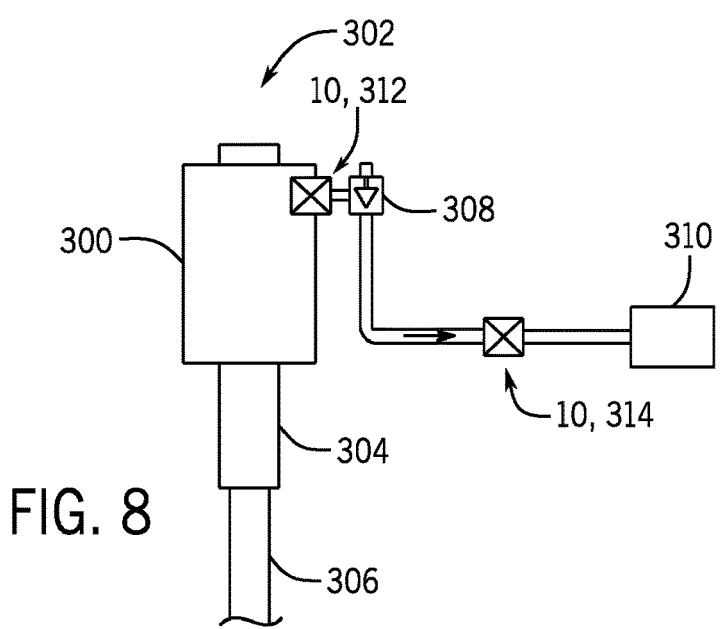
FIG. 8 is a schematic diagram showing multiple GISDS positioned at various locations about a surface tree of a surface production system, in accordance with an embodiment of the present disclosure.

FIG. 8 is a schematic elevation diagram showing multiple GISDS 10 positioned at various locations within a surface tree 300 of a surface production system 302, in accordance with an embodiment of the present disclosure. The surface tree 300 may include various fluid control devices, such as various valves (e.g., isolation valves), and may be mounted on a wellhead 304 positioned above a conductor pipe 306 (e.g., casing) that extends into the wellbore. As shown, a choke valve 308 may be provided to control a flow rate of a fluid (e.g., production fluid) extracted from a well via the surface production system 302 to a downstream processing system 310 (e.g., manifold and/or processing devices). In certain embodiments, GISDS 10 may be positioned on one or both sides (e.g., an upstream and/or a downstream side) of the choke valve 308. A first GISDS 10, 312 upstream of the choke valve 308 may enable detection of water content and/or free gas at the surface tree 300. As shown, a second GISDS 10, 314 is positioned downstream of the choke valve 308 and may enable analysis of the fluid under reduced pressure (e.g., as compared to the first GISDS 10, 312). In certain embodiments, the second GISDS 10, 314 may be configured to detect free gas, which may in turn be compared to the free gas detected by the first GISDS 10, 312 and/or to various acceptable predetermined ranges and/or baseline data and/or used (e.g., in algorithms by a control system) to detect changes in content of the fluid produced by the well over time, for example. In some embodiments, data from the illustrated GISDS 10 may advantageously indicate gas-in-solution and/or other characteristics of the fluid before the fluid is comingled or mixed with fluids from other wells. Such data may enable a controller or an operator to adjust downstream processing (e.g., to handle gas, water, oil, etc.), to select various wells and/or mix fluid produced by different wells at different times to produce a desired comingled flow, or the like, which in turn may improve field production efficiency and reduce costs.

Figure 9:
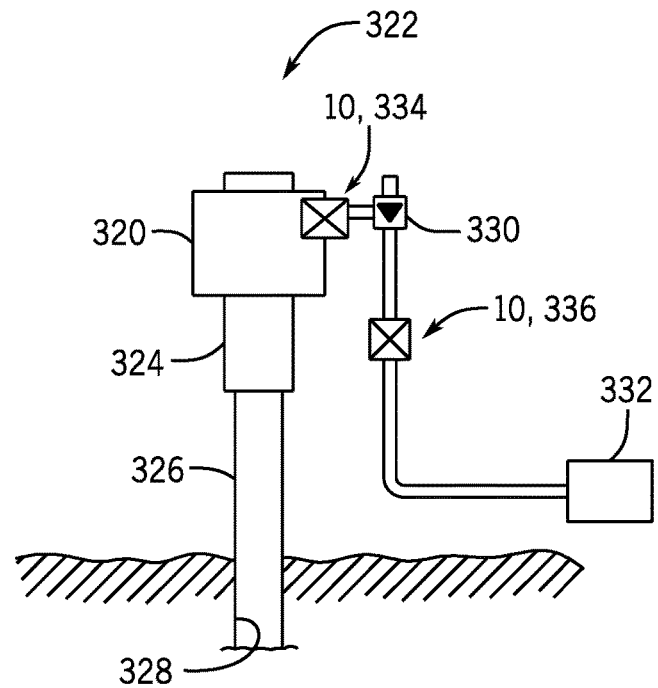
FIG. 9 is a schematic diagram showing multiple GISDS positioned at various locations about a subsea tree of a subsea production system, in accordance with an embodiment of the present disclosure.

FIG. 9 is a schematic elevation diagram showing multiple GISDS 10 positioned at various locations within a subsea tree 320 of a subsea production system 322, in accordance with an embodiment of the present disclosure. The subsea tree 320 may include various fluid control devices, such as various valves (e.g., isolation valves), and may be mounted on a wellhead 324 positioned above a conductor pipe 326 (e.g., casing) that extends into a wellbore 328. As shown, a choke valve 330 may be provided to control a flow rate of a fluid (e.g., production fluid) extracted from a well via the subsea production system 322 to a downstream processing system 332 (e.g., manifold and/or processing devices). In certain embodiments, GISDS 10 may be positioned on one or both sides (e.g., an upstream and/or a downstream side) of the choke valve 330. A first GISDS 10, 334 upstream of the choke valve 330 may enable detection of gas-in-solution at the subsea tree 320. As shown, a second GISDS 10, 336 is positioned downstream of the choke valve 330 and may enable analysis of the fluid under reduced pressure (e.g., as compared to the first GISDS 10, 334). In a similar manner as discussed above with respect to FIG. 8, the second GISDS 10, 336 may be configured to detect free gas, which may in turn be compared to the free gas detected by the first GISDS 10, 312 and/or to various acceptable predetermined ranges and/or baseline data and/or used (e.g., in algorithms by a control system) to detect changes in content of the fluid produced by the well over time, for example. As discussed above, such data may advantageously indicate characteristics of the fluid before the fluid is comingled or mixed with fluids from other wells and may enable a controller or an operator to adjust downstream processing (e.g., to handle gas, water, oil, etc.), to select various wells and/or mix fluid produced by different wells at different times to produce a desired comingled flow, or the like, which in turn may improve field production efficiency and costs.

Figure 10:
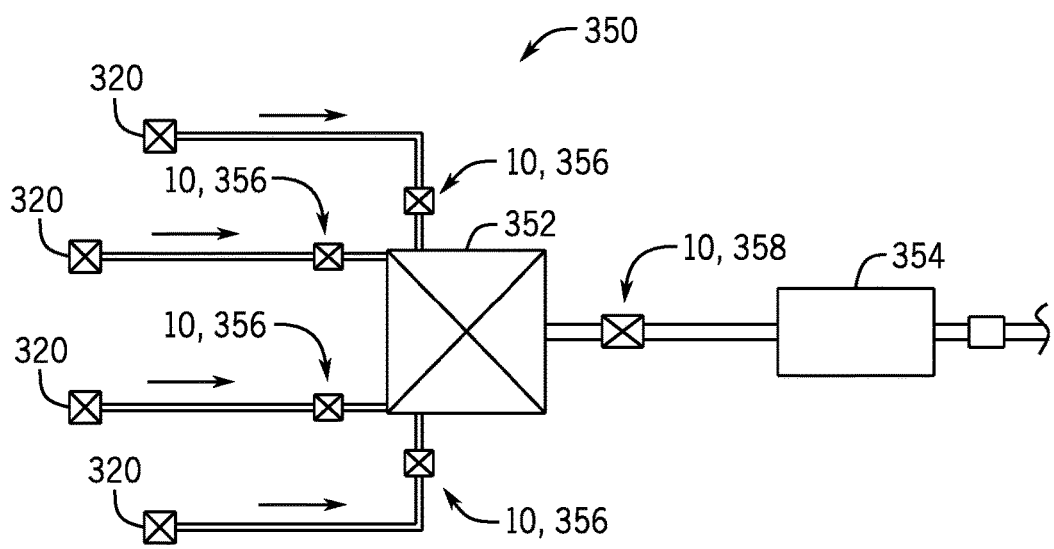
FIG. 10 is a schematic diagram showing multiple GISDS positioned about a subsea field, in accordance with an embodiment of the present disclosure.

FIG. 10 is a schematic plan diagram showing multiple GISDS 10 positioned about a subsea field 350, in accordance with an embodiment of the present disclosure. As shown, the subsea field 350 includes multiple subsea trees 320 each configured to extract fluid through a respective wellbore. The multiple subsea trees 320 are coupled to a manifold 352 where the fluid extracted by the multiple subsea trees 320 is comingled or mixed together, and the fluid then flows to a subsea processing system 354 (e.g., having separation devices, pumping devices, etc.) to process the fluid and to direct the fluid toward a riser extending to the sea surface, for example. As discussed above with respect to FIG. 9, multiple GISDS 10 may be provided proximate to each subsea tree 320. Additionally or alternatively, GISDS 10 may be positioned on one or both sides of the manifold 352 (e.g., on an upstream side and/or on a downstream side of the manifold 352). For example, as shown, respective first GISDS 10, 356 are positioned proximate to the manifold 352 and between each subsea tree 320 and the manifold 352, and a second GISDS 10, 358 is positioned between the manifold 352 and the subsea processing system 354.

Figure 11:
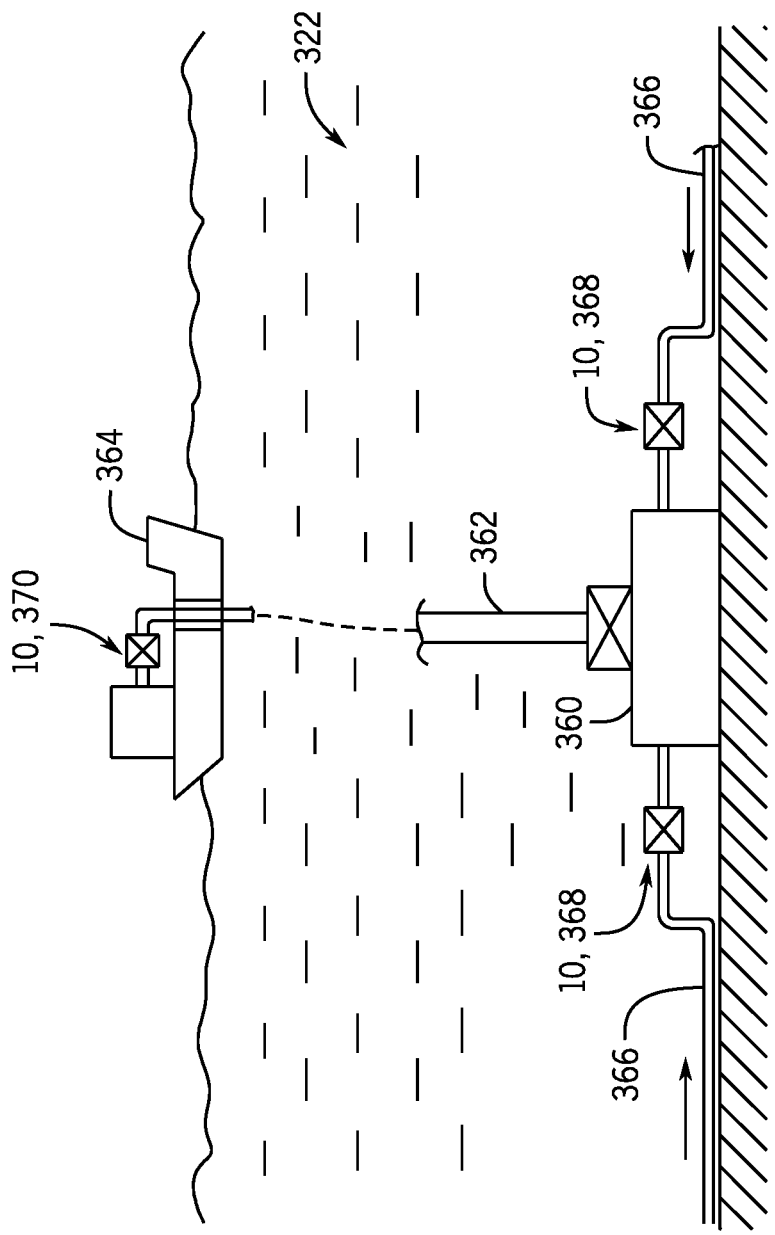
FIG. 11 is a schematic diagram showing multiple GISDS positioned about a subsea production system, in accordance with an embodiment of the present disclosure.

FIG. 11 is a schematic elevation diagram showing multiple GISDS 10 positioned about a portion of the subsea production system 322, in accordance with an embodiment of the present disclosure. As discussed above with respect to FIGS. 9 and 10, the system 322 may include multiple subsea trees 320, the manifold 352, the fluid processing system 354, and respective GISDS 10 positioned about these components. As shown in FIG. 11, the system 322 may also include a riser base 360 supporting a riser 362 that extends to a surface production platform or vessel 364. In operation, fluid may flow through pipelines 366 (e.g., from the subsea trees 320, manifold 352, and/or fluid processing system 354) to the riser base 360, which directs the fluid through the riser 362 to the platform 364. In addition to or as an alternative to the GISDS 10 illustrated in FIGS. 9 and 10, the system 322 may include respective GISDS 10, 368 along each pipeline 366 proximate to the riser base 360 and between the riser base 360 and the fluid processing system 354 and/or the GISDS 10, 370 at the platform 364 (e.g., a surface GISDS 10, 370 located above the sea surface).

In some circumstances, as fluid flows through extended pipelines often used in subsea production systems 322 and subsea fields 350, frictional losses may cause pressure to drop and free gas to increase. Additionally or alternatively, the fluid may partially separate, resulting in a multi-phase flow (e.g., two-phase flow, liquid and gas flow) and/or phase slugs. Thus, it may be desirable to position multiple GISDS 10 throughout the subsea field 350 and/or through the subsea production system 322, as shown in FIGS. 9-11, in order to monitor characteristics of the fluid at different locations and/or to detect changes as the fluid flows through the subsea field 350 and/or the subsea production system 322 and to predict and/or to anticipate the free gas that will be present at downstream locations under reduced pressure, for example. The data from the GISDS 10 shown in FIGS. 8-11 may enable a controller or an operator to adjust downstream processing (e.g., to handle gas, water, oil, etc.), to select various wells and/or mix fluid produced by different wells at different times to produce a desired comingled flow, or to take other appropriate actions, which in turn may improve field production efficiency and costs.

Figure 12:
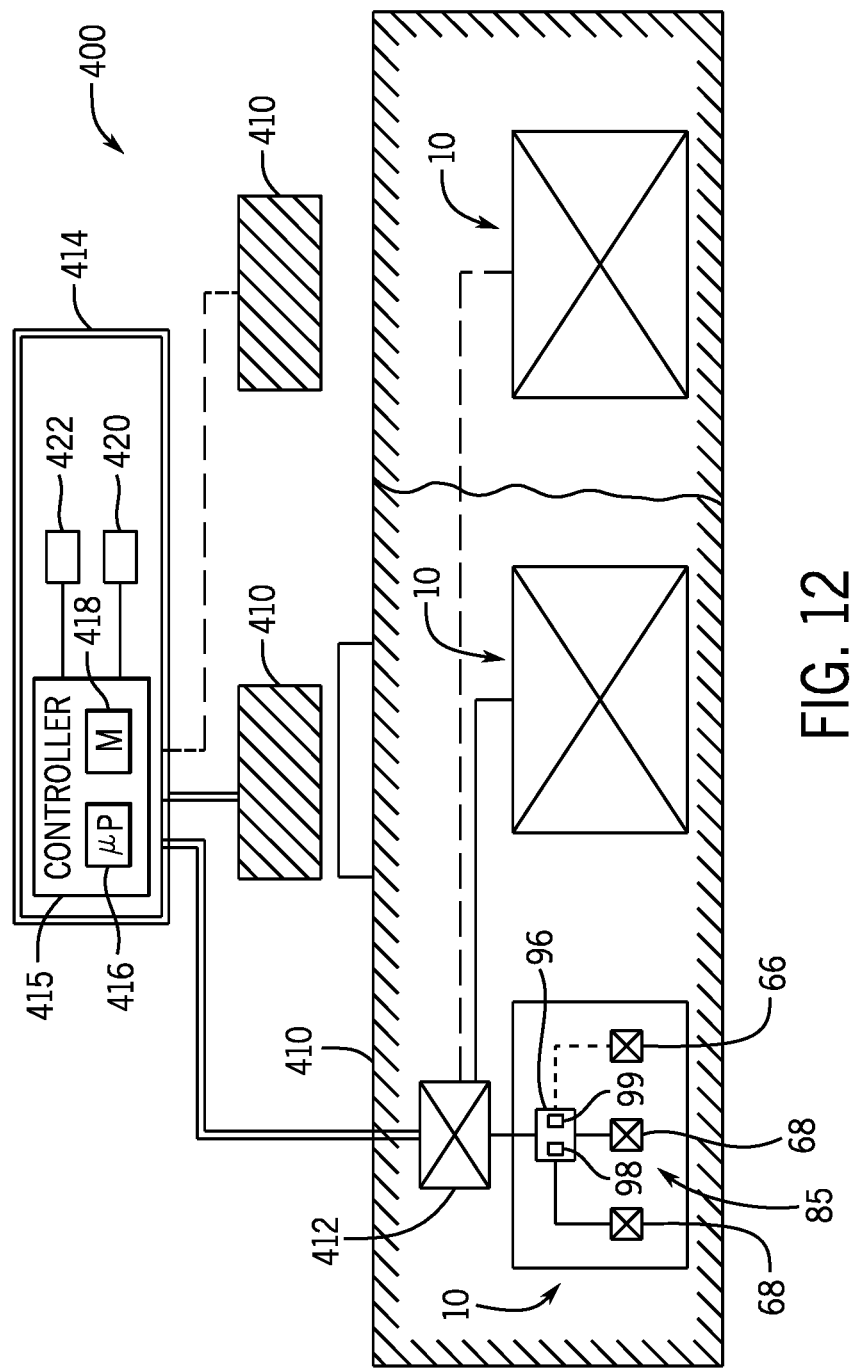
FIG. 12 is a block diagram of a control system for use with multiple GISDS, in accordance with an embodiment of the present disclosure.

FIG. 12 is a block diagram of a control system 400 for use with multiple GISDS 10, in accordance with an embodiment of the present disclosure. The control system 400 is an electronic control system having electronic controllers with processors and memory devices. As shown, each GISDS 10 may include or be coupled to a respective controller 96, which may include electrical circuitry configured to receive and/or to process signals from the sensors 85 of the GISDS 10 and/or to provide control signals to certain components of the GISDS 10, for example. In the illustrated embodiment, the controller 96 includes the processor 98 and the memory device 99. The illustrated GISDS 10 includes the acoustic transceiver 66 and multiple pressure and/or temperature sensors 68 to facilitate discussion; however, it should be understood that the GISDS 10 may include any of a variety of sensors 85, including those noted above with respect to FIG. 2, for example.

In certain embodiments, multiple GISDS 10 (e.g., the GISDS 10 used to monitor one subsea production system 322, the GISDS 10 used to monitor a particular portion of a drilling or production system, etc.) may be arranged into a module 410 having a module multiplexer (MUX)/de-multiplexer (DEMUX) 412 to provide signals to and/or to receive signals from a remote station 414 (e.g., at the drilling floor, at the platform at the sea surface, etc.). As shown, the remote station 414 may be coupled to multiple modules 410 (e.g., via a respective module MUX/DEMUX 412). In certain embodiments, the remote station 414 may include an electronic controller having a processor 416, a memory device 418, and/or an output device 420, such as a speaker and/or a display, to provide an output based on the signals generated by the sensors within the GISDS 10. For example, in some embodiments, the remote station 414 may be configured to provide an alarm, a prompt or recommendation via the output device 420, and/or a control signal, in the same manner discussed above with respect to the controller 96 of FIG. 2. In some embodiments, the remote station 414 includes a user interface 422 that may enable an operator to control and/or to provide instructions to the GISDS 10, such as to activate certain sensors 85 within the GISDS 10, control the pump 76, actuate valves 52, 57, 59 of FIG. 2 and/or valves 89, 91 of FIG. 3 to initiate or to enable a monitoring session, or the like. As noted above, the processing and/or control features of the control system 400 may be distributed between various processors (e.g., the processor 98, the processor 416, etc.) in any suitable manner.

Figure 13:
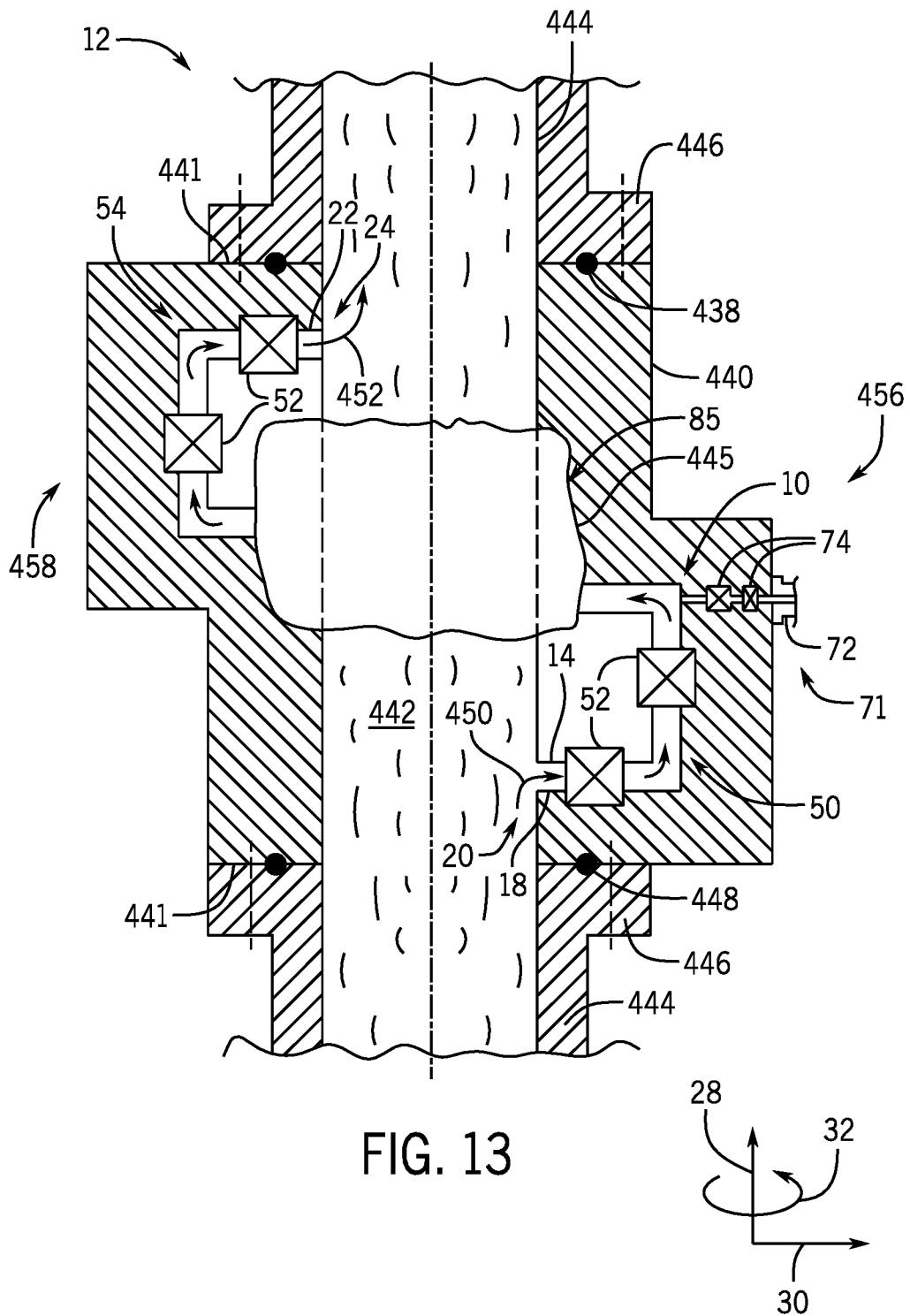
FIG. 13 is a cross-sectional side view of a GISDS positioned within a housing, in accordance with an embodiment of the present disclosure.
Figure 14:
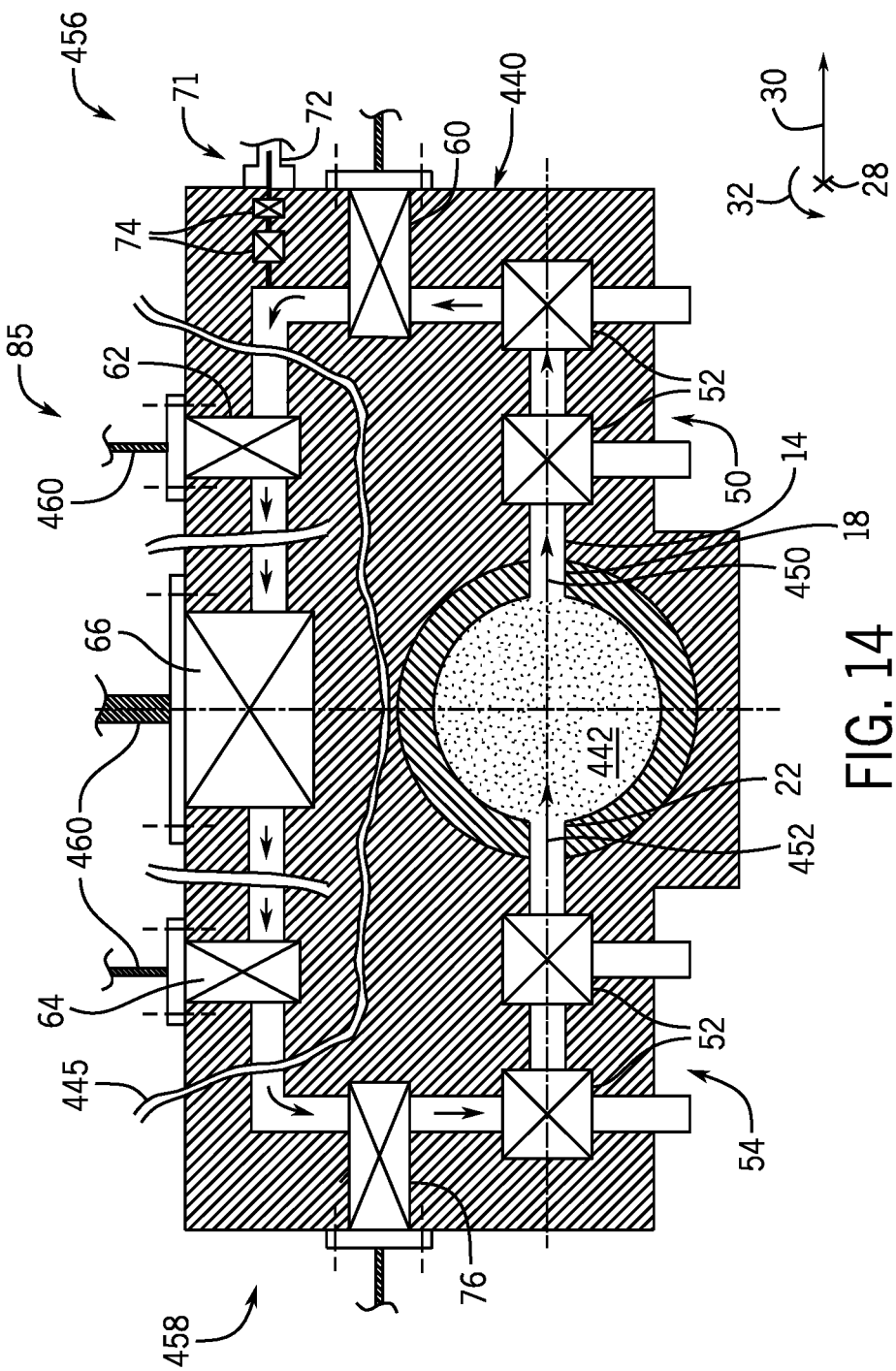
FIG. 14 is a top view of a GISDS positioned within a housing, in accordance with an embodiment of the present disclosure.

FIG. 13 is a cross-sectional side elevation view of an embodiment of a GISDS 10 positioned within a housing 440 (e.g., GISDS housing) and FIG. 14 is a top plan view of an embodiment of a GISDS 10 positioned within the housing 440, in accordance with an embodiment of the present disclosure. In the illustrated embodiment, the housing 440 is an annular structure having a central bore 442 configured to align with (e.g., coaxial) and/or form part of the conduit 12 through which the fluid flows. Such a configuration may enable the housing 440 to be positioned between and to be coupled (e.g., via fasteners, such as threaded fasteners) to pipe sections 444 of the conduit 12. For example, as shown in FIG. 13, the housing 440 has mounting portions 441 (e.g., axial end surfaces) coupled to respective connectors 446 (e.g., flange or riser coupling) of the pipe sections 444, and gaskets 448 (e.g., annular gaskets) are positioned between the housing 440 and the respective connectors 446 to contain the fluid within the conduit 12 and the housing 440. Such a configuration may be particularly suitable for use with relatively large conduits 12, such as a drilling riser.

The components of the GISDS 10 may be arranged in any suitable manner within the housing 440. As shown in FIG. 13, the first end 18 of the channel 14 extends from the first portion 20 of the conduit 12, and the second end 22 of the channel 14 is coupled to the second portion 24 of the conduit 12. The first end 18 and the second end 22 of the channel 12 may be spaced apart from one another along the axial axis 30 and/or the circumferential axis 34. For example, in the illustrated embodiment, the first end 18 and the second end 22 of the channel 14 are spaced apart from one another along both the axial axis 30 and the circumferential axis 34. As shown in FIG. 14, in the illustrated embodiment, the first end 18 and the second end 22 of the channel 14 are diametrically opposed to one another across the bore 442 of the housing 440. As shown, the first isolation assembly 50 is positioned proximate to the first end 18 of the channel 14, and the second isolation assembly 54 may be positioned proximate to the second end 22 of the channel 14. In the illustrated embodiments, the flush line 72 and the flush line valves 74 are coupled to the channel 14, and the pump 76 is positioned downstream of the piston assembly 60 and the sensors 85 and proximate to the second isolation assembly 54. The piston assembly 60 and multiple sensors 85 are positioned along the channel 14 between the first and second isolation assemblies 50, 54, with the piston assembly 60 and at least some of the sensors 85 within line 445 in FIGS. 13 and 14 for purposes of image clarity. As shown in FIG. 14, the illustrated GISDS 10 includes the acoustic transceiver 66 and the pressure and/or temperature sensor 68 for image clarity and to facilitate discussion; however, it should be understood that the GISDS 10 may include any of a variety of sensors 85, including those discussed above with respect to FIG. 2, for example. In the illustrated embodiments, the piston assembly 60 and at least some of the multiple sensors 85 are positioned along a portion of the channel 14 that extends in the radial direction 32 between a first side 456 (e.g., lateral side) and a second side 458 (e.g., lateral side) of the housing 440. As shown in FIG. 14, the various components (e.g., the sensors 85, the pump 76, the valves 52, etc.) of the GISDS 10 may be positioned within the housing 440 to enable connection to a cable 460 (e.g., an electrical cable) that is coupled to the controller (e.g., the controller 96) positioned outside of the housing 440. However, in some embodiments, the controller may be positioned within the housing 440, and the cables 460 may extend through the housing 440 between the components and the controller such that the GISDS 10 is entirely contained within and/or supported by the housing 440.

In operation, the fluid may flow from the conduit 12 into the channel 14, as shown by arrow 450. When the first isolation assembly 50 is in an open position (e.g., the valves 52 are in an open position), the fluid may flow into the channel 14 and through or past the sensors 85 of the GISDS 10 to enable the sensors 85 to monitor characteristics of the fluid. When the second isolation assembly 54 is in the open position, the fluid may return to the conduit, as shown by arrow 452.

Figure 15:
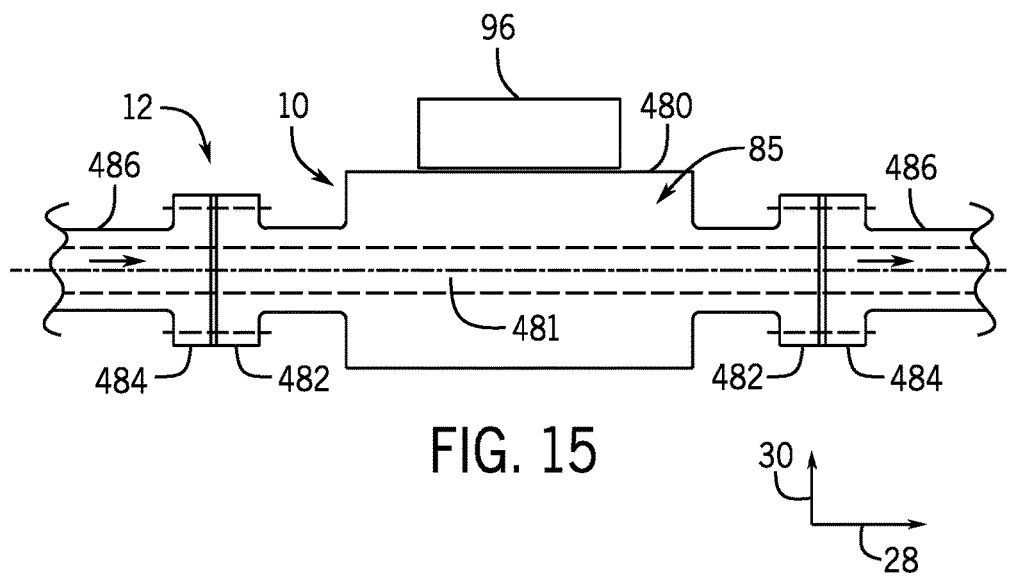
FIG. 15 is side view of a GISDS positioned within a housing, in accordance with an embodiment of the present disclosure.

The GISDS 10 may be supported within a housing having any of a variety of configurations. For example, FIG. 15 is side view of a GISDS 10 positioned within a housing 480, in accordance with an embodiment of the present disclosure. As shown, the housing 480 is an annular housing having a central bore 481 and includes connectors 482 (e.g., flanges) that are configured to mate with respective connectors 484 (e.g., flanges) of adjacent pipe sections 486 of the conduit 12. Such a configuration may enable the housing 480 to be positioned between and to align with pipe sections 486 (e.g., coaxial) to enable fluid flow through the conduit 12. Such a configuration may be particularly suitable for smaller conduits 12, such as choke lines, kill lines, and/or production pipelines, for example. The various components of the GISDS 10, including the piston assembly 60 and the sensors 85 and other components shown in FIG. 2, may be positioned within the housing 480.

Figure 16:
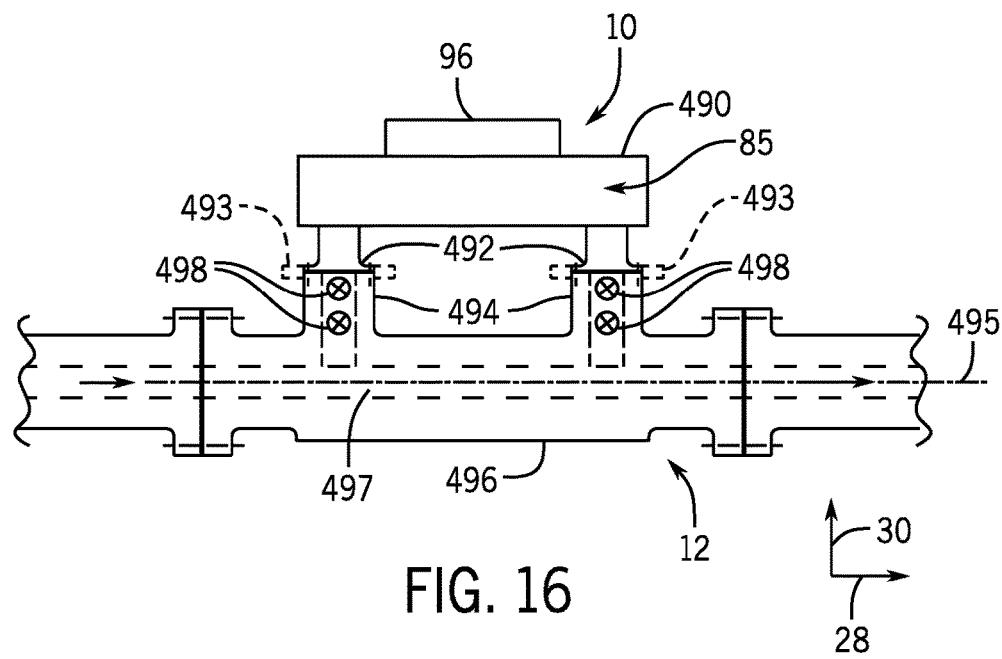
FIG. 16 is a side view of a GISDS positioned within a retrievable housing, in accordance with an embodiment of the present disclosure.

FIG. 16 is a side view of a GISDS 10 positioned within a retrievable housing 490, in accordance with an embodiment of the present disclosure. In the illustrated embodiment, the housing 490 includes connectors 492 (e.g., flanges) that are configured to mate with sections 494 (e.g., valve-supporting sections) extending radially outward from the pipe section 496 that forms the conduit 12. In certain embodiments (e.g., subsea GISDS 10), additional connectors 493 may be provided to facilitate coupling the housing 490 to the sections 494 of the pipe section 496. As shown, valves 498 may be positioned within the sections 494 to control fluid flow between the conduit 12 and the housing 490. In the illustrated embodiment, the housing 490 is offset or spaced apart from the conduit 12 in the radial direction 30 (e.g., side-mounted with laterally-extending side mounts or laterally offset from a central axis 495 of a bore 497 of the conduit 12). Such a configuration may enable the housing 490 and the GISDS 10 to be separated from the conduit 12 and retrieved with a cap on the sections 494 without disrupting or stopping flow through the conduit 12. The housing 490 may be particularly useful for monitoring fluid flow through manifolds and/or subsea equipment, as the housing 490 may enable the GISDS 10 to be removed for inspection, maintenance, repair, and/or replacement, without moving the large, heavy equipment. The various components of the GISDS 10, including the piston assembly 60, the sensors 85, and the other components shown in FIG. 2, may be positioned within the housing 490.

Figure 17:
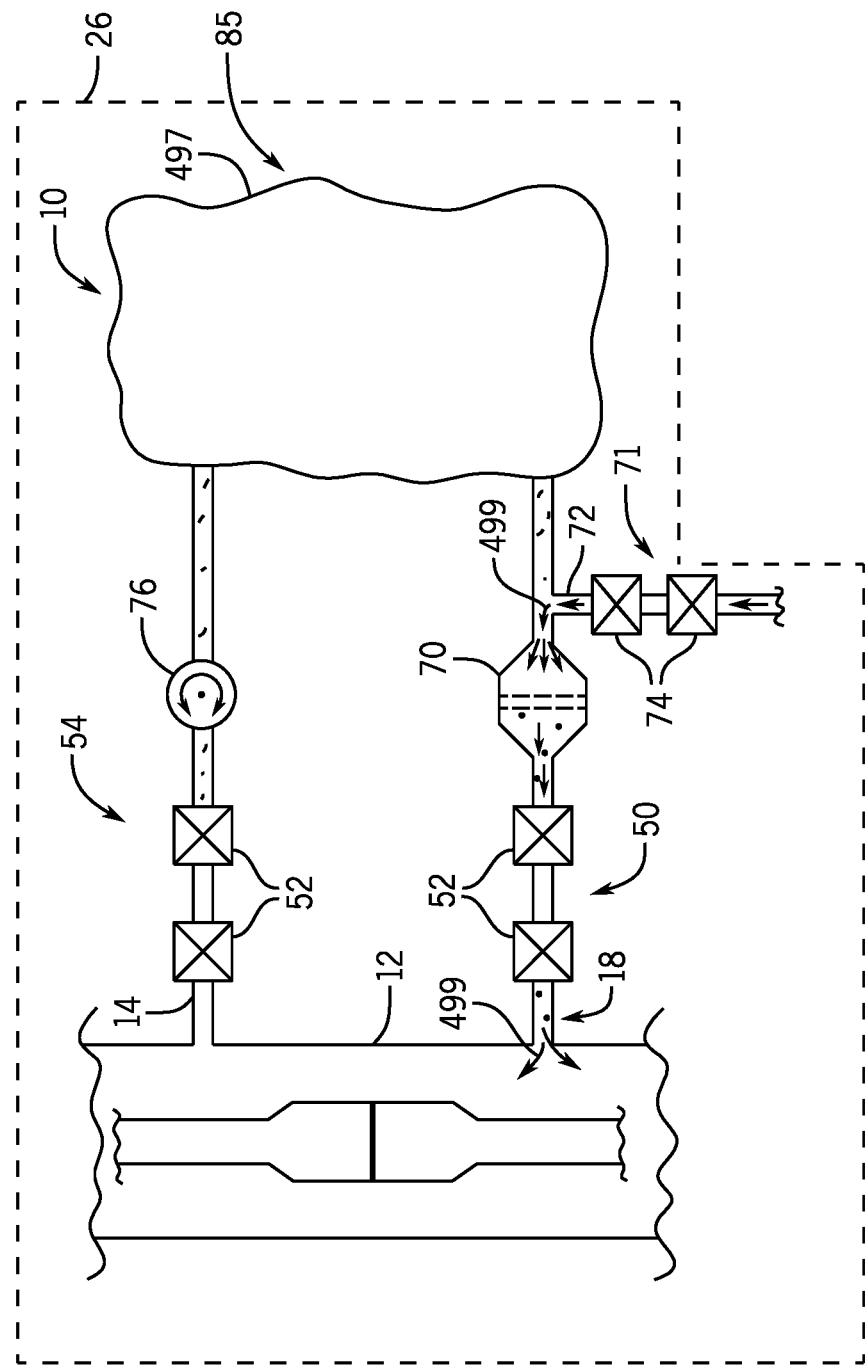
FIG. 17 is a schematic diagram illustrating a GISDS during a flushing process, in accordance with an embodiment of the present disclosure.

FIG. 17 is a schematic diagram illustrating a GISDS 10 during a flushing process, in accordance with an embodiment of the present disclosure. In the illustrated embodiment, the first isolation assembly 50 is in an open position, the second isolation assembly 54 is in a closed position, and the flush line valves 74 are in an open position. In the illustrated configuration, the flush line fluid may flow from the flush line 72, through the flush line valves 74, and through the filter 70 into the conduit 12, as shown by arrows 499, thereby flushing or cleaning the filter 70 (e.g., dislodging particulate matter from the filter 70) and a portion of the channel 14 between the flush line 72 and the first end 18 of the channel 14. In some embodiments, a series of flushes with various flush fluids may be carried out (e.g., a first flush process to remove wax and a second flush process to remove hydrates). Various other components, such as the piston assembly 60 and the sensors 85, may be positioned within the housing 26, such as in an area 497.

Figure 18:
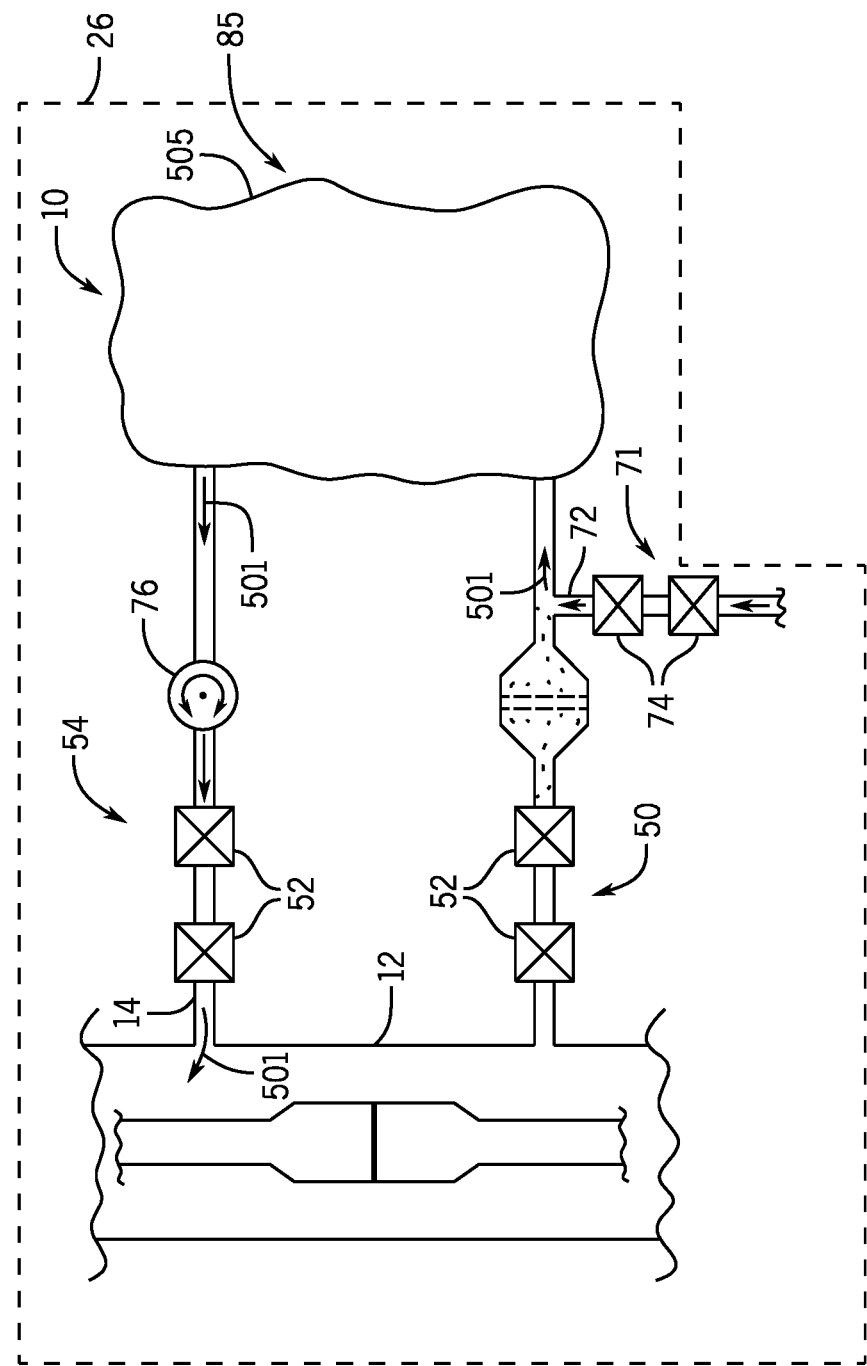
FIG. 18 is a schematic diagram illustrating the GISDS of FIG. 17 during a sensor calibration process, in accordance with an embodiment of the present disclosure.

FIG. 18 is a schematic diagram illustrating the GISDS 10 of FIG. 17 during a sensor calibration process, in accordance with an embodiment of the present disclosure. In the illustrated embodiment, the first isolation assembly 50 is in a closed position, the second isolation assembly 54 is in an open position, and the flush line valves 74 are in an open position. In the illustrated configuration, the flush line fluid may flow from the flush line 72, through the flush line valves 74, past the sensors 85 positioned along the channel 14, such as within an area 505, and through the second isolation assembly 54 into the conduit 12, as shown by arrows 501, thereby flushing or cleaning the sensors 85 and/or the portion of the channel 14 between the flush line 72 and the second end 22 of the channel 14. Such a configuration may also facilitate a sensor calibration process. For example, the flush fluid may have certain known properties or characteristics. As the flush fluid passes the sensors 85, the sensors 85 may measure respective characteristics, which may be compared to the known characteristics and/or baseline data, and the sensors 85 may be calibrated based on this comparison (e.g., coefficients or algorithms used to process signals generated by the sensors 85 during the monitoring process may be adjusted or selected based on this comparison during the calibration process). In some embodiments, a series of calibration processes with the same or different flush fluids may be carried out to improve accuracy of the calibration.

Figure 19:
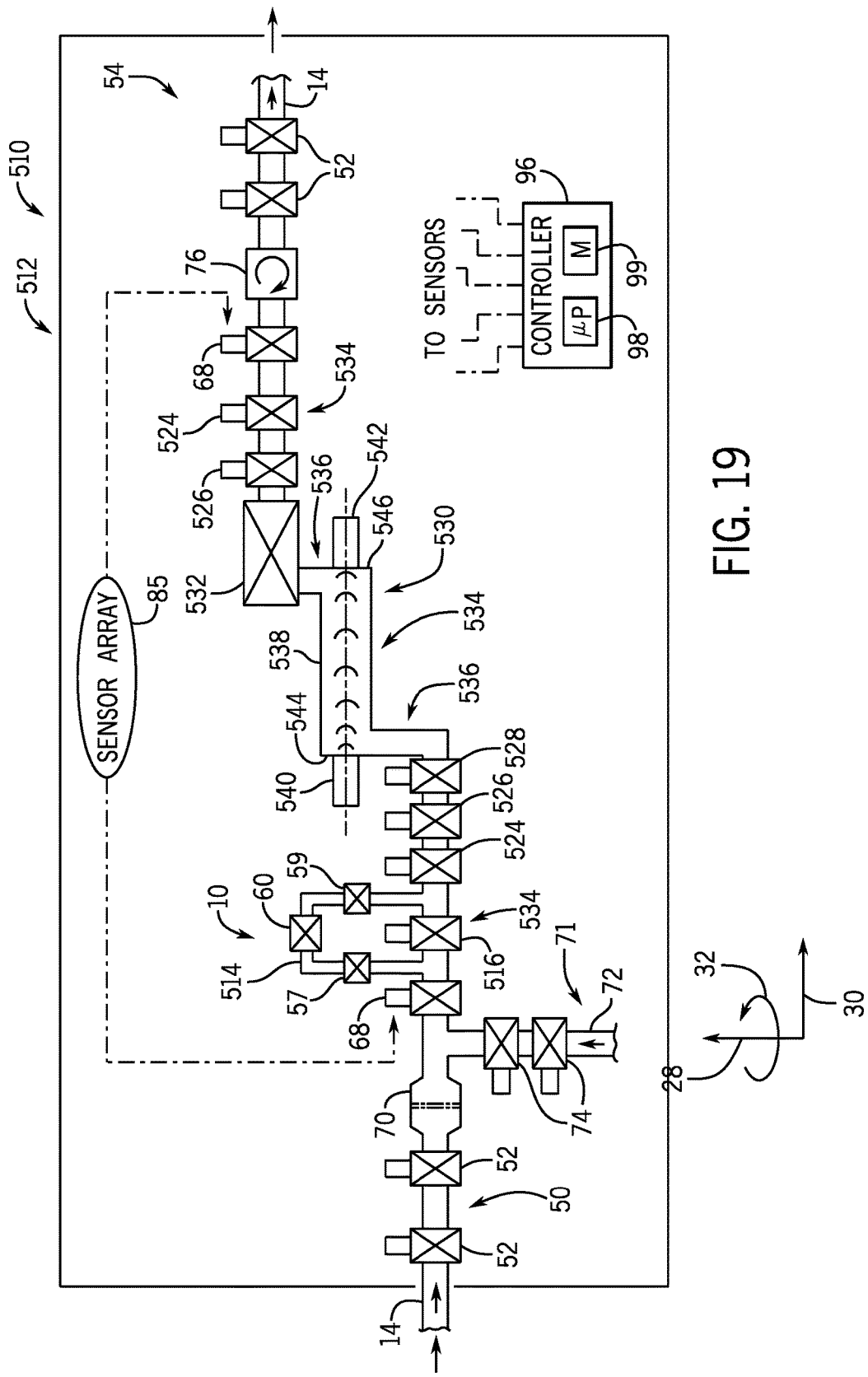
FIG. 19 is schematic diagram of a GISDS package including the GISDS utilized with a fluid analysis monitoring systems (FAMS) having multiple sensors, in accordance with an embodiment of the present disclosure.

FIG. 19 is a schematic diagram of an embodiment of a GISDS package 510 having the GISDS 10 that includes or is utilized with a fluid analysis monitoring systems (FAMS) 512. In the illustrated embodiment, the FAMS 512 includes multiple sensors 85 positioned along the channel 14, and certain components of the GISDS 10 (e.g., the valves 57, 59 and/or the piston assembly 60) are positioned along a GISDS passageway 514 that extends from the channel 14. As shown, the GISDS passageway 514 forms a loop to extract fluid from the channel 14 at one location and to return the fluid to the channel 14 at another location. The illustrated embodiment includes a shut-off valve 516, which may move between an open position to enable flow across the shut-off valve 516 and a closed position to block flow across the shut-off valve 516 and to divert fluid into the GISDS passageway 514. For example, when the shut-off valve 516 is in the closed position, fluid may be diverted into the GISDS passageway 514, and the valves 57, 59 may be controlled as discussed above with respect to FIGS. 2-4 to contain a fixed volume of the fluid within the chamber 62 of the piston assembly 60 and to monitor for the presence of gas-in-solution.

In the illustrated embodiment, the monitoring system 510 includes a variety of sensors, such as a conductivity sensor 524 configured to monitor the conductivity of the fluid, a capacitance sensor 526 configured to monitor the capacitance of the fluid, a chemical sensor 528 (e.g., gas composition sensor or carbon dioxide sensor) configured to monitor the chemical levels (e.g., gas composition or carbon dioxide levels) within the fluid, an ultrasonic sensor assembly 530 configured to monitor attenuation of acoustic waves (e.g., ultrasonic waves) within the fluid, and a spectrometer assembly 532 (e.g., optical, infrared, radiation, mass, gamma-ray, nuclear magnetic resonance [NMR], and/or diffraction grating spectrometer assembly or sensor) configured to monitor absorption of light and/or energy by the fluid. Such characteristics measured by the sensors 85 may in turn be utilized (e.g., by the controller 96) to determine a free gas content, a dielectric constant, a density, a viscosity, an oil content, and/or a water content of the fluid. For example, the conductivity, the capacitance, and/or the attenuation of the acoustic waves may be indicative of the density and/or the free gas content of the fluid. In certain embodiments, the light and/or energy absorption may be indicative of the free gas content, the water content, and/or the oil content of the fluid. Thus, in certain embodiments, signals generated by sensors 85 may be indicative of and used to determine gas-in-solution, a pressure, a temperature, a conductivity, a capacitance, a dielectric constant, a chemical level, a gas composition, a carbon dioxide level, an ultrasonic frequency, an ultrasonic velocity, attenuation of acoustic waves, absorption of light and/or energy, a density, a viscosity, a free gas content, an oil content, and/or a water content, for example. Such characteristics may be utilized (e.g., by a controller or by an operator) to determine appropriate outputs and/or actions. For example, certain characteristics (e.g., increase in free gas, reduced density, or the like) may indicate an influx of formation fluid within drilling mud or a potential "kick" event, and other characteristics (e.g., oil content and/or water content) may provide valuable information regarding the composition of produced fluids. It should be understood that the sensors 85 shown in FIG. 19 are provided as examples and are not intended to be limiting, and that any of a variety of sensors 85 may be utilized within the monitoring system 510, including the sensors 85 discussed above, as well as viscosity sensors, density sensors, electrodes, and/or any other suitable sensors configured to monitor and to obtain signals indicative of fluid parameters, including a pressure, a temperature, a conductivity, a capacitance, a dielectric constant, a chemical level, a gas composition, a carbon dioxide level, an ultrasonic frequency, an ultrasonic velocity, attenuation of acoustic waves, absorption of light and/or energy, a density, a viscosity, a free gas content, an oil content, and/or a water content, for example. Furthermore, the sensors 85 may be positioned at any location along the channel 14 and/or along the channel 514 and/or positioned to monitor the fluid within the chamber 62 of the piston assembly 60. As discussed in more detail below, the signals generated by the sensors 85 may be provided to a controller (e.g., such as the controller 96) having electrical circuitry configured to process the signals to detect gas-in-solution, for example.

It should be understood that any suitable type and any suitable number (e.g., 1, 2, 3, 4, 5, 6, 7, 8, 9, 10 or more) of each type of sensor 85 may be provided within the monitoring system 510. In certain embodiments, the monitoring system 510 may include more than one of each type of sensor 85. For example, as shown, the monitoring system 510 includes two pressure and/or temperature sensors 68, two conductivity sensors 524, and two capacitance sensors 526. Such a configuration may provide increased accuracy and/or reliability of measurements, as well as enable determination of a quality metric indicative of the accuracy and/or reliability of the measurements (e.g., based on a variation between respective measurements at a downstream sensor 85 and an upstream sensor 85 within the monitoring system 510). Furthermore, the sensors 85 may be positioned to directly contact the fluid within the channel 14 and/or isolated from the fluid. For example, the pressure and/or temperature sensor 68 may be positioned within the flow path of the fluid within the channel 14 to directly contact the fluid, while the ultrasonic sensor assembly 530 may be positioned outside of the flow path of the fluid within the channel 14.

In some embodiments, the width or the diameter 80 of the channel 14 may vary based on the sensors 85, such that the channel 14 has a particular, optimized width or diameter 80 (e.g., that enables accurate and/or reliable monitoring of the fluid) for each sensor 85 at the sensor's location along the channel 14. For example, the width or the diameter 80 may be selected to enable the sensor 85 to protrude a particular, desired distance into the channel 14. In some embodiments, the monitoring system 510 10 may include sensors 85 having a transmitter and receiver pair, and the width or the diameter 80 may be selected to enable the receiver to receive signals from the transmitter.

Additionally or alternatively, the channel 14 within the monitoring system 510 may include portions that extend in different directions. For example, in the illustrated embodiments, the channel 14 includes portions 534 that extend in a first direction (e.g., radial direction 30) and portions 536 that extend in a second direction (e.g., axial direction 28). In some embodiments, the portions 534, 536 of the channel 14 may be arranged to form a chamber 538 to facilitate placement of sensors 85 at various orientations relative to fluid flow and/or to facilitate certain measurements. For example, as shown, the chamber 538 is formed by one portion 534 that extends in the first direction and is positioned between two portions 536 that extend in the second direction. Such a configuration may enable placement of sensors 85 at one or both ends of the chamber 538. In the illustrated embodiment, the monitoring system 510 includes the ultrasonic sensor assembly 530, which includes a transmitter 540 configured to emit an acoustic wave and a receiver 542 configured to receive the acoustic wave emitted by the transmitter 540. As shown, the transmitter 540 is positioned at a first end 544 of the chamber 538 and the receiver 542 is positioned at a second end 546 of the chamber 538, opposite the transmitter 540 at the first end 542. A length of the chamber 538 may enable the receiver 542 to receive waves from the transmitter 540, and furthermore, the positioning of these components at opposed ends 542, 546 of the chamber 538 enables the acoustic signal to pass through a sample of the fluid within the chamber 538 in a direction generally parallel to the fluid flow, which may facilitate monitoring of frequency shifts, amplitude changes, and/or the attenuation of the acoustic wave. It should be understood that, in certain embodiments, the ultrasonic sensor assembly 530 may be positioned to emit acoustic waves in a direction generally transverse or perpendicular to the fluid flow, or at any of a variety of other angles (e.g., between approximately 5 to 85, 20 to 60, or 30 to 50 degrees) relative to the fluid flow. In some embodiments, data from the sensors 85 may be provided to the controller 96, which is configured to process the data (e.g., using one or more algorithms, including machine learning algorithms, predictive models, or the like) to determine gas-in-solution, as well as other characteristics of the fluid, for example. As shown, the monitoring system 510 includes the isolation assemblies 50, 52, the filter 70, the pump 76, the flush system 71, and it should be understood that the monitoring system 510 and the GISDS 10 may include any of the features disclosed herein. It should be understood that the monitoring system 510, or certain features of the monitoring system 510, depicted in FIG. 19 may be utilized in the various drilling and production systems shown in FIGS. 6-12 and/or in the various housings shown in FIGS. 13-18 in addition to or in lieu of the components of the GISDS 10 illustrated in each of these figures.

Figure 20:
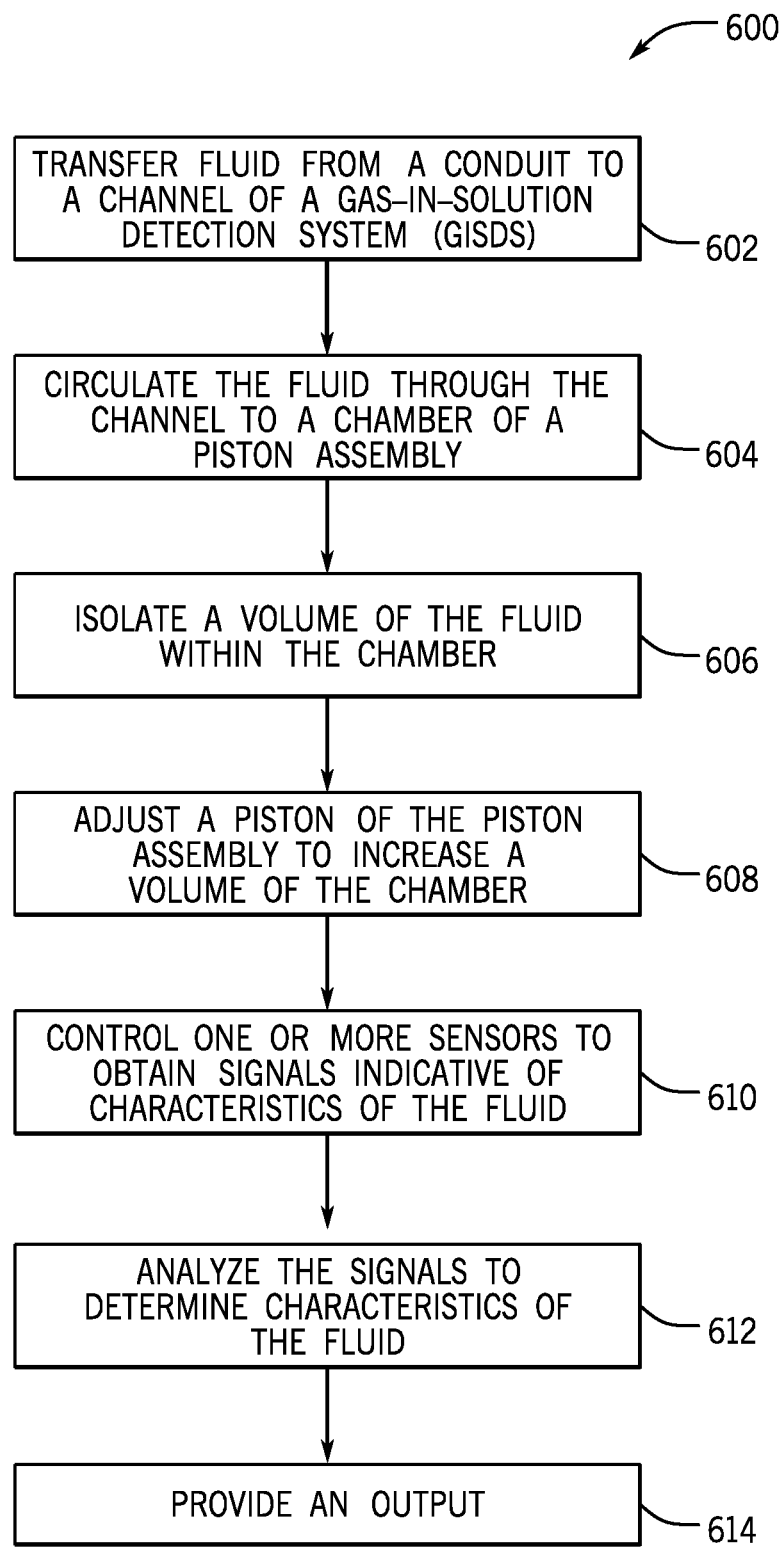
FIG. 20 is a flow diagram of a method for operating a GISDS, in accordance with an embodiment of the present disclosure.

FIG. 20 is a flow chart illustrating a method 600 for monitoring fluid within a drilling system and/or a production system, in accordance with the present disclosure. The method 600 includes various steps represented by blocks. It should be noted that the method 600 may be performed as an automated procedure by a system, such as the control system 400 of FIG. 12. Although the flow chart illustrates the steps in a certain sequence, it should be understood that the steps may be performed in any suitable order and certain steps may be carried out simultaneously, where appropriate. Further, certain steps or portions of the method 600 may be performed by separate devices. For example, a first portion of the method 600 may be performed by the processor 98, while a second portion of the method 600 may be performed by a separate processing device, such as the processor 416 (FIG. 12). As noted above, the steps of the method 600 for monitoring the fluid may be initiated automatically (e.g., according to a program stored in the memory device 99 or the memory device 418) and/or in response to operator input (e.g., via user interface 422).

The method 600 may begin when fluid is transferred from the conduit 12 to the channel 14 of the GISDS 10, in step 602. In certain embodiments, the fluid may be transferred from the conduit 12 to the channel 14 when a processor (e.g., the processor 98, the processor 416, or the like) controls the valves 52 of the first isolation assembly 50 and/or the second isolation assembly 54 to move from a closed position to the open position, for example. In step 604, the processor may control the pump 76 or another fluid control device may circulate fluid into and through the channel 14 and/or adjust a flow rate of the fluid through the channel 14 to the chamber 62 of the piston assembly 60.

In step 606, a volume of fluid may be isolated within the chamber 62, such as via controlling valves 57, 59 to closed positions via the processor. In step 608, the piston 64 of the piston assembly 60 may be withdrawn from the chamber 62, thereby expanding the volume of the chamber 62 and reducing pressure within the chamber 62. In some embodiments, the piston 64 may be driven by the processor controlling valves 89, 91 (FIG. 4) of a hydraulic drive system to provide hydraulic fluid to various chambers of the piston assembly 60, as discussed above.

In step 610, the processor may control one or more sensors 85 of the GISDS 10 to obtain signals indicative of characteristics of the fluid within the channel 14 and/or within the chamber 62. For example, the processor may control the acoustic transducer 66 to obtain data related to velocity of acoustic waves (e.g., ultrasonic waves) and/or attenuation of acoustic waves within the chamber. The processor may obtain data related to pressure and/or temperature within the chamber 62 and/or at other locations within the GISDS 10 from the one or more pressure and/or temperature sensors 68. As discussed above, the GISDS 10 may include any of a variety of sensors 85 configured to monitor characteristics of the fluid.

In step 612, the signals generated by the one or more sensors 85 may be received at and/or processed by the processor to determine characteristics of the fluid. For example, such data may be indicative of a presence of free gas within the chamber 62, a phase transition from gas-in-solution to free gas under the reduced pressure within the chamber 62, or the like. Thus, such data may enable the processor to detect the presence or the absence of gas-in-solution in the fluid extracted from the conduit 12. In some embodiments, the data may be processed to determine an amount or a ratio of gas-in-solution in the fluid extracted from the conduit 12. Furthermore, the signals from various sensors 85 may be processed to determine a dielectric constant, a density, a viscosity, a free gas content, an oil content, a water content of the fluid, a conductivity, a capacitance, and/or an attenuation of acoustic waves, energy, or light, for example. In some embodiments, the processor may analyze the sensor data, such as by comparing the gas-in-solution and/or other characteristics to predetermined acceptable ranges and/or to baseline data. For example, in certain embodiments, the processor may determine a change (e.g., absolute value and/or percentage) of the gas-in-solution and/or one or more other characteristics by comparing sensor data from one or more sensors 85 of one GISDS 10 to sensor data from one or more sensors 85 of another GISDS 10.

In step 614, the processor may provide an output (e.g., a visual or audible output via the user interface 422 or a control signal) based on detected gas-in-solution and/or determined characteristics. For example, the processor may be configured to provide a visual or audible output that indicates the presence or the absence of gas-in-solution, a trend or a change in the gas-in-solution over time, a rate of change of the gas-in-solution over time, a change in the detected gas-in-solution as compared to a predetermined acceptable range and/or a baseline measurement, or the like. In some embodiments, the processor may be configured to initiate an alarm and/or provide a prompt. In some embodiments, the output may include control signals to control various components of the GISDS 10 and/or the drilling and/or production system. In this way, the processor may be configured to provide information related to the fluid and/or facilitate appropriate action.

The examples provided herein are not intended to be limiting and any and all of the features shown and described with respect to FIGS. 1-20 may be used in any combination with one another (e.g., positions of sensors and components with the GISDS 10, positions of GISDS 10 within the drilling and/or production system, housings, conduits, or the like). Furthermore, each GISDS 10 may be configured to perform any and all functions disclosed herein, including controlling any and all of the various sensors 85 and components of the GISDS 10, monitoring any and all of the characteristics disclosed herein, processing signals, providing outputs, communicating (e.g., exchanging signals) with other GISDS 10 and/or various components of a control system (e.g., the control system 400), for example. Each GISDS 10 may be configured to compare sensor data at one location with all other locations and/or sensor data at the same location, and the comparison may be made between the same or different sensors (and measured parameters), at same or different time (e.g., real time, same time, previous time, etc.). For example, the GISDS 10 may compare sensor data at all locations for one or more parameters at a common time (e.g., whether real time or previous time). In some embodiments, each GISDS 10 may be configured to compare sensor data to baseline data, which may be any of a variety of suitable predetermined acceptable ranges, thresholds, and/or baseline measurements such as post-calibration measurements, measurements under ideal conditions, modeled measurements, known parameters or characteristics of the fluid, current or historical measurements at the same or different GISDS 10, and/or average measurements and/or median measurements taken across GISDS 10 and/or across time, or the like. The GISDS 10 may be configured to compare sensor data in a sequence of locations in a direction of flow (e.g., through the entire drilling and/or production system or portions of the flow path). Furthermore, GISDS 10 may be positioned at/in upstream and/or downstream locations of each illustrated component in FIGS. 1-19.

While the disclosure may be susceptible to various modifications and alternative forms, specific embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the disclosure as defined by the following appended claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . ." or "step for [perform]ing [a function] . . .", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A fluid monitoring system, comprising:
    a channel comprising a first end configured to be fluidly coupled to a first portion of a conduit for a fluid to flow from the conduit into the channel and a second end configured to be fluidly coupled to a second portion of the conduit to enable return of the fluid from the channel into the conduit;
    an actuator assembly positioned along the channel and configured to isolate a portion of the fluid within a chamber of the actuator assembly, wherein the actuator assembly is configured to expand a volume of the chamber to reduce a pressure while the portion of the fluid is within the chamber to facilitate identification of an indicator of dissolved gas within the fluid; and
    an acoustic transducer configured to emit acoustic waves into the chamber of the actuator assembly, wherein the acoustic transducer is configured to facilitate identification of the indicator of the dissolved gas within the fluid based on a reflection of the acoustic waves received by the acoustic transducer.

2. The system of claim 1, comprising a first isolation assembly positioned between the first end of the channel and the actuator assembly and a second isolation assembly positioned between the actuator assembly and the second end of the channel.

3. The system of claim 1, wherein the conduit comprises at least one of a choke line, a kill line, a subsea pipeline, or a surface pipeline.

4. The system of claim 1, wherein the conduit comprises a subsea drilling riser.

5. The system of claim 1, comprising a pressure sensor configured to monitor a pressure within the chamber of the actuator assembly to facilitate identification of the indicator of dissolved gas within the fluid.

6. The system of claim 1, comprising a temperature sensor configured to monitor a temperature within the chamber of the actuator assembly to facilitate identification of the indicator of dissolved gas within the fluid.

7. The system of claim 1, comprising a pump positioned along the channel between the actuator assembly and the second end of the channel, wherein the pump is configured to adjust a flow rate of the fluid through the channel.

8. The system of claim 1, comprising a controller and multiple sensors, wherein the controller is configured to receive signals indicative of respective characteristics of the fluid from the multiple sensors including the acoustic transducer, to analyze the signals to detect the indicator of dissolved gas within the fluid, and to provide an instruction to actuate a control device based on detection of the indicator of dissolved gas within the fluid.

9. The system of claim 1, comprising a housing configured to be coupled to the conduit, wherein the channel is formed in the housing and the actuator assembly is positioned within the housing.

10. The system of claim 1, wherein the actuator assembly comprises a piston assembly having a piston configured to move within a cylinder to expand the volume of the chamber.

11. The system of claim 10, wherein the acoustic transducer is configured to emit the acoustic waves toward a surface of the piston, and wherein the surface of the piston is configured to direct the reflection of the acoustic waves toward the acoustic transducer.

12. The system of claim 1, wherein the acoustic transducer is an ultrasonic transducer.

13. A system configured to detect dissolved gas in a fluid within a conduit of a mineral extraction system, comprising:
    an actuator assembly configured to receive and to isolate a portion of the fluid within a chamber of the actuator assembly, wherein the actuator assembly is configured to expand a volume of the chamber to reduce a pressure while the portion of the fluid is within the chamber; and
    one or more sensors configured to monitor characteristics of the portion of the fluid within the chamber to facilitate identification of an indicator of dissolved gas within the fluid, wherein the one or more sensors comprises an acoustic transducer configured to emit acoustic waves into the chamber of the actuator assembly, wherein the acoustic transducer is configured to facilitate identification of the indicator of the dissolved gas within the fluid based on a reflection of the acoustic waves received by the acoustic transducer.

14. The system of claim 13, comprising a channel configured to extend from a side wall of the conduit and to flow the portion of the fluid from the conduit to the chamber of the actuator assembly, wherein the channel comprises a first end configured to extend from a first portion of the side wall of the conduit to enable flow of the fluid from the conduit into the channel and a second end configured to extend from a second portion of the side wall of the conduit to enable return of the fluid from the channel into the conduit.

15. The system of claim 13, wherein the actuator assembly is positioned at a subsea location.

16. The system of claim 13, wherein the conduit comprises at least one of a subsea pipeline or a subsea drilling riser.

17. The system of claim 13, wherein the one or more sensors comprise a pressure sensor configured to monitor a pressure within the chamber of the actuator assembly and a temperature sensor configured to monitor a temperature within the chamber of the actuator assembly to facilitate identification of the indicator of dissolved gas within the fluid.

18. A method of monitoring a fluid within a conduit of a mineral extraction system, comprising:
    transferring the fluid from the conduit into a channel via a first end of the channel;
    isolating a portion of the fluid within a chamber of an actuator assembly positioned along the channel;
    driving a piston of the actuator assembly to expand a volume and to reduce a pressure of the chamber while the portion of the fluid is isolated within the chamber;
    operating an acoustic transducer to monitor a characteristic of the portion of the fluid within the chamber, wherein operating the acoustic transducer comprises emitting acoustic waves into the chamber of the actuator assembly; and
    determining whether gas-in-solution, free gas, or a combination thereof, is present within the fluid based on the characteristic based on a reflection of the acoustic waves received by the acoustic transducer.

19. The method of claim 18, comprising reinjecting the fluid back into the conduit via a second end of the channel.

20. The method of claim 18, comprising calculating a bubble point of the fluid within the chamber, using a processor.

* * * * *